United States Patent [19]

Hoots et al.

[11] Patent Number: 5,435,969

[45] Date of Patent: *Jul. 25, 1995

[54] MONITORING WATER TREATMENT AGENT IN-SYSTEM CONCENTRATION AND REGULATING DOSAGE

[75] Inventors: John E. Hoots, St. Charles; Martin R. Godfrey, Elburn, both of Ill.

[73] Assignee: Nalco Chemical Company, Naperville, Ill.

[*] Notice: The portion of the term of this patent subsequent to Feb. 14, 2012 has been disclaimed.

[21] Appl. No.: 219,063

[22] Filed: Mar. 29, 1994

[51] Int. Cl.$^6$ .................................................. G01N 21/77
[52] U.S. Cl. ........................................ 422/14; 422/3; 422/16; 422/18; 422/19; 436/6; 436/56; 436/172
[58] Field of Search ............... 422/12, 13, 14, 15, 422/16, 18, 19, 119, 3; 436/6, 56, 72, 79, 81, 83, 100, 103, 111, 139, 172

[56] References Cited

U.S. PATENT DOCUMENTS

| | | | |
|---|---|---|---|
| 4,176,007 | 11/1979 | Jeffers et al. | 436/172 X |
| 4,783,314 | 11/1988 | Hoots et al. | 422/3 |
| 4,963,267 | 10/1990 | Hoots et al. | 210/701 |
| 4,966,711 | 10/1990 | Hoots et al. | 210/697 |
| 4,992,380 | 2/1991 | Moriarty et al. | 436/55 |
| 5,006,311 | 4/1991 | Hoots et al. | 422/62 |
| 5,035,806 | 7/1991 | Fong et al. | 210/701 |
| 5,041,386 | 8/1981 | Pierce et al. | 436/50 |
| 5,120,661 | 6/1992 | Baker et al. | 436/164 |
| 5,128,419 | 7/1992 | Fong et al. | 525/351 |
| 5,132,096 | 7/1992 | Hoots et al. | 422/82.09 |
| 5,166,074 | 11/1992 | Vessey et al. | 422/17 X |
| 5,171,450 | 12/1992 | Hoots | 210/701 |
| 5,178,771 | 1/1993 | Hayashibe et al. | 436/175 X |
| 5,200,106 | 4/1993 | Hoots et al. | 252/181 |
| 5,216,086 | 6/1993 | Fong et al. | 525/351 |
| 5,260,386 | 11/1993 | Fong et al. | 525/340 |
| 5,266,493 | 11/1993 | Young | 436/55 |
| 5,277,135 | 1/1994 | Dubin | 110/345 |
| 5,278,074 | 1/1994 | Rao et al. | 436/52 |
| 5,282,379 | 2/1994 | Harder et al. | 73/29.01 |

OTHER PUBLICATIONS

Doude Van Troostwijk, "Tracer Improves the Metering of Water Treatment Chemicals", *Polytech. Tijdschar,* 1993, 48(5), 70–1.

Hoots et al. "Use of Fluorescent Tracer Signficantly Improves Control of Cooling Water Treatment", *Mater. Perform.* (1992), 31(2), 46–51.

*Primary Examiner*—Robert J. Warden
*Assistant Examiner*—Robert Carpenter
*Attorney, Agent, or Firm*—Robert A. Miller; James J. Drake; Patricia A. Charlier

[57] ABSTRACT

A concentration-fluctuation responsive regulation of water treatment agent feed is achieved by adding an incipient to a sample whereby a concentration indicator is formed. Such a concentration indicator comprises a combination of the incipient reagent and a substantially nonfluorescent water treatment agent. The concentration indicator is then monitored by fluorescence analysis of the sample to determine at least one fluorescence emission value that can be correlated to an in-system concentration of the water treatment agent. The fluorescence emission value measured in then correlated to the in-system concentration of the water treatment agent.

18 Claims, No Drawings

MONITORING WATER TREATMENT AGENT IN-SYSTEM CONCENTRATION AND REGULATING DOSAGE

TECHNICAL FIELD OF THE INVENTION

The present invention is in the technical field of regulating the in-system concentration of water treatment agents and/or system operation, particularly the in-system concentration of water treatment agents in industrial water systems, such as cooling water systems, boiler water systems, water reclamation/purification systems, water systems of manufacturing processes and the like, by analysis of one or more component(s) of treatment program so as to increase the efficiency of the water treatment agents and/or operation of systems in which they are used.

BACKGROUND OF THE INVENTION

The concentration of water treatment agents in industrial water systems is traditionally controlled based on intermittent measurements of the concentration of the water treatment agent(s) in the water of the system and/or the concentration of the specie or condition targeted by the water treatment agent (the target specie). The measurements of the concentration of the water treatment agent(s) in the water of the system, and any responsive in-system concentration adjustments, are commonly based only on occasional grab samples, taken for instance once or twice per shift (a shift commonly encompassing about 8 to 12 hours of system operating time) or once every several days.

Traditional methods of determining the concentration of a water treatment agent in a water system are usually somewhat cumbrous and/or protracted, and/or provide results that are merely estimates and/or variable (for instance, dependent upon a person's laboratory technique). Long time delays typically exist between changes in system operation and a compensating change in treatment dosage. Analyses for water treatment agents have heretofore generally been made using classical (wet chemistry) techniques, at times accompanied by water flowmeter and/or conductivity readings. A sample of water from the system is taken and a wet chemical test is performed. The conventional wet chemical tests include titrations or manual addition of reagents to the water sample that react with the species of interest to form a turbid or colored solution that can be measured with an optical spectrophotometer. The turbidity or intensity of the color is proportional to the concentration of the species of interest. For example, phosphate concentrations are determined by a spectrophotometric (colorimetric) test. Concentrations of pyrophosphate and organic phosphorus compounds are determined using the same spectrophotometric test after a digestion (reversion) step.

Many of the conventional analytical methods for measuring the concentration of water treatment agents are susceptible to interference from other materials in the water sample, in some instances methods are nonexistent, and/or are subjective, such as visual observation of color change. For instance, colorimetric analysis of orthophosphate is a commonly used technique, but it is susceptible to turbidity interference.

The more accurate a conventional manual (grab sample) analysis technique, the more protracted that technique can be. Feedback information can at times even be days behind the sampling and hence of little value in providing data from which a dosage-regulation response can be determined. Moreover, the concentration of the water treatment agent may well have changed during the elapsed interval.

Estimating the in-system concentration for a water treatment agent, and in turn regulating the feed of the treatment agent to meet a target in-system concentration, is further complicated by other imprecise evaluations of operating parameters. The rate at which the water treatment agent is being fed to the industrial water system, and/or other operating parameters having an influence on the in-system concentration of the water treatment, may defy precise or accurate measurement. The readings and/or settings on feed equipment and/or lines are seldom unquestionably reliable. Fluctuations in the concentration of the water treatment agent may stem from a variety of system conditions, such as dilution when other materials are charged to the system, concentration by evaporation, steam generation or other means, unaccounted loss of fluid from the system, and the like, some of which parameters may not be accurately known.

Even when accurate indications of the mass or volume of a water treatment agent feed delivered to a system are available, and accurate water treatment agent residual concentrations are available, if the residual concentration determinations are based on grab or intermittent samples, any extrapolation therefrom to a value for the system consumption of the water treatment agent is based on fragmentary data and outdated information. A change in the in-system concentration might not be detected until it has had a significant impact on treatment agent and system performance. The regulation of in-system concentration will be at least in part a response after the active agent's performance has changed. When the detection of system consumption change is delayed, the responsive regulation of a treatment agent's in-system concentration will invariably be late and system performance may suffer. When the responsive regulation of in-system concentration is late, underfeeding or overfeeding of the treatment agent routinely will occur to some extent between the time the system's consumption for the water treatment agent changed and the time the treatment agent in-system concentration is adjusted and/or system operating parameter (e.g., alkalinity) adjustment.

In an industrial water system plant the use of any estimated, variable, intermittent, fragmentary or historic data (for instance data from a method that inherently has a long response delay time or is non-selective, such as conductivity analysis) severely diminishes the sensitivity of any concentration-fluctuation responsive regulation of the water treatment agent feed rate and/or diminishes the ability to follow changes in the in-system concentration with appropriate compensations to the water treatment agent feed rate.

Conventional procedures for regulating water treatment agent in-system concentration are further complicated by other imprecise evaluations of operating parameters. The rates at which the water treatment agent is being fed to and/or removed from the industrial water system and/or other operating parameters having an influence on the in-system concentration of the water treatment, may defy precise measurement unless inert tracers and selective analytical methods are used. The readings and/or settings on feed and blowdown equipment and/or lines are seldom unquestionably reliable and often complicated by multiple sources of blowdown and makeup and changes in composition of those water samples. Fluctuations in the concentrations in the target species and the water treatment agent may stem from a variety of system conditions, such as dilution when other materials are charged to the system, concentration by evaporation or other means, unaccounted loss of fluid from the system and the like, some of which parameters may not be accurately known. Generally all sources of water intake and loss, and all sources of water treatment agent intake and loss, cannot be known precisely and continuously unless inert tracers and selective analytical methods are used.

A sensitive, selective, and rapid concentration-fluctuation responsive control of water treatment agent in-system concentration would render most any industrial water system more efficient. A sensitive and rapid consumption responsive control of water treatment agent in-system concentration would render most any industrial water system more efficient. Overfeeding of a water treatment agent is unnecessarily expensive, may at times diminish the recycling potential of waste water discharged from the system, and may also at times impair system performance. Underfeeding of a water treatment agent almost inevitably impairs system performance, the imbalance between an underfed water treatment agent and its target species leading to higher degrees of deleterious effect(s) from which relief is sought by the water treatment. In some water systems an imbalance between the concentrations of water treatment agents charged to the system and the system's water conditions and/or target species can severely diminish the efficiency of the system. For instance, an imbalance in water treatment agent concentration can diminish the efficiency of a temperature conditioning performance (such as heat exchange) or a heat transfer performance (such as steam generation), or diminish the performance of a process to which a water system is adjuvant.

It is an object of the present invention to provide a method or process for regulating the in-system concentration of one or more water treatment agents to a water system that can be conducted on-site in a very short time period. It is an object of the present invention to provide a method or system for regulating the in-system concentration of a water treatment agent in an industrial water system that is concentration-fluctuation responsive and can be conducted on-site, preferably on a continuous basis. It is an object of the present invention to provide a method or system for regulating the in-system concentration of a water treatment agent in an industrial water system that is system consumption responsive and can be conducted on-site, preferably on a continuous basis. It is an object of the present invention to provide in an industrial water system one or more monitorings of in-system concentration for water treatment agents on-site in a very short time period, preferably on a continuous basis. It is an object of the present invention to provide in an industrial water system at least one monitoring of an in-system concentration for a water treatment agent in the water system, together with the monitoring of a water treatment agent's system consumption, to provide a sensitive regulation of such in-system concentration on-site in a very short time period, preferably at least in part on a continuous basis. These and other objects of the present invention are described in detail below.

DISCLOSURE OF THE INVENTION

The present invention provides a concentration-fluctuation responsive management (regulation or control) of a water treatment agent in-system concentration(s) and/or system operating parameter(s), for example by regulating water treatment agent feed, which includes the monitoring of an in-system water treatment agent concentration indicator by fluorescence analysis. The present invention provides a process for the regulation of the feed rate of at least one substantially nonfluorescent water treatment agent ("WTA"), based on the value of the in-system concentration of that treatment agent, comprising monitoring a fluorescent characteristic of at least one in-system WTA concentration indicator ("concentration indicator") that is a combination of an incipient reagent and a WTA. The WTA may be any WTA which is combinable with a suitable reagent to form an in-system WTA-concentration indicator which has a fluorescent characteristic that can be correlated to the value of the WTA's in-system concentration. That fluorescent characteristic is monitored, preferably on a continuous basis, by at least one fluorescence analysis method and the results of such monitoring(s) are correlated with a regulation of the feed rate of such treatment agent.

In preferred embodiments, the system consumption of the WTA is also monitored by monitoring the concentration of an inert tracer added to the system in proportion to the WTA. The system consumption for a water treatment agent can be determined from the following Formula Formula $C_1 - C_2 = SC$ wherein $C_1$ is the water treatment agent concentration added to the system as determined by correlation to the concentration of an associated inert tracer (added in known proportion with the water treatment agent), $C_2$ is the observed concentration of the water treatment agent determined by monitoring the concentration indicator, and SC is the system consumption upon the water treatment agent or, in other words, selective impact(s) upon in-system concentration of the water treatment agent that does not effect the inert tracer's in-system concentration.

More preferably, such inert tracer is monitored by fluorescence analysis, for instance by using a treatment product to which an inert fluorescence tracer has been added in known proportion to the WTA, and determining the level of such tracer within the system. In preferred embodiments, the present invention further includes the monitoring of an inert tracer, which together with the monitoring of the WTA indicator is used to determine system consumption for the WTA, which is described in detail below.

In further preferred embodiments, the effects of any adjustments to the WTA's in-system concentration are tracked by continued monitoring of the in-system WTA concentration indicator, preferably in combination with continued monitoring of the system consumption. In other preferred embodiments, the system consumption readings are used to measure system performance or troubleshoot problems with system performance.

PREFERRED EMBODIMENTS OF THE INVENTION

The concentration of water treatment agents as solutes in the water of a water system will fluctuate by virtue of a wide variety of mechanisms, one or more of which may be occurring at any given point in time. A WTA concentration will decrease when WTA-containing deposits form, when the WTA is consumed during metal corrosion, when the WTA is degraded in the system, and when other like WTA-consuming phenomena occur. A WTA concentration will also decrease when WTA-containing fluid leaves the system and is replaced with fluid having a lesser WTA-concentration. A WTA concentration will increase when WTA-containing deposits are dissolved, when fluid having a lesser WTA-concentration leaves the system, for instance by evaporation, steam generation and like mechanisms, and when other like WTA-releasing or WTA-concentrating phenomena occur. A plurality of WTA-concentration increasing phenomena and/or WTA-concentration decreasing phenomena can be occurring at the same time.

One WTA-increasing mechanism, of course, is the intentional feed of the WTA to the water system. As mentioned above, the controls on a typical industrial additive-feed mechanism (based on manual control or indirect analysis methods) seldom add a WTA with a high degree of precision. A more precise measurement of the effect of feed rate on the in-system concentration can be made when a tracer is added to the water system in known proportion to the WTA, which is described in more detail below.

In some instances, the primary concentration-decreasing and concentration-increasing phenomena (outside of normal system controls such as WTA feed, water blowdown, water make-up and the like) are respectively the formation and dissolution of WTA-containing deposits. The formation and dissolution of WTA-containing deposits, in turn, might be directly related to the water treatment program performance. Primary goals of such a program might be to minimize deposition and/or corrosion within the water system. In such instances, the present invention's regulation of WTA in-system concentration based on the monitoring of the WTA system demand is also a regulation of WTA in-system concentration based on water treatment program performance. Such instances are preferred embodiments of the present invention. When the regulation of WTA in-system concentration is based on water treatment program performance, the WTA concentration adjustment may be broadened to a treatment-program concentration regulation. The monitoring may measure the depletion or excess of one or more WTA's, but that in turn will be a measure of an insufficient or excess amount of a plurality of WTA's or even an entire multi-WTA treatment program.

The present invention comprises the measuring of the concentration of at least one WTA in the water of an industrial water system by monitoring a WTA-concentration indicator in a water sample from the system. By the term "monitoring" is meant herein, unless expressly indicated otherwise, the determination of at least one fluorescence characteristic of an in-system WTA concentration indicator and/or an inert tracer in a sample from a water system, and correlating that characteristic to a value that can be equated to in-system concentration of the WTA and/or tracer. By the term "regulating" is meant herein, unless expressly indicated otherwise, the setting and/or the adjustment of a system control means, for instance the feed rate (feed forward, feed back) of the WTA to the system, which determines at least in part the concentration of the WTA in a water system. Such monitoring(s) and/or regulating can be conducted on a singular, intermittent, semi-continuous or continuous basis, and preferably at least the monitoring(s), and more preferably both the monitoring(s) and regulating, is/are conducted on-site (at the site of the industrial water system plant) on a substantially continuous basis.

The present invention includes the regulating of at least one WTA in-system concentration based on the in-system concentration of, or system consumption for, the WTA by employing the information provided by the monitoring of the in-system WTA concentration indicator alone or in combination with the monitoring of an associated inert tracer. The water treatment in-system concentration is regulated by the process of the present invention based on the present value of the WTA in-system concentration or system consumption, and not on estimated, fragmentary or historic data. The present invention can be considered a method that tracks, and/or obviates the need to quantify, the multitude of influences on the water treatment agent concentration and system consumption, such as the introduction of a target specie to the system with makeup water or other added materials, mixing of multiple streams, contamination, leaks between systems, leaks from the system, other dilutions and concentrations, releases of WTA into the water from known and unknown sources, losses of WTA from the water by known and unknown mechanisms and the like.

Variations in the in-system concentration can occur by virtue of numerous operating conditions such as pH, bulk water temperature, heat-exchanger skin temperature and heat flux, water flow velocity, and ions. The rate at which the WTA is entering and/or leaving and/or being generated in an industrial water system cannot wholly be predicted or controlled. An industrial water system commonly has unknown sources of material intake and/or losses and/or chemical conversions. The optimal monitoring of a water treatment agent concentration is to quantify the concentration in a water system, rather than attempting to estimate its change in concentration based on other parameters. The method of the present invention can determine the concentration of one or more in-system WTA concentration from in-system WTA concentration indicator values that can be correlated thereto, using one or more fluorescence analysis techniques.

The present invention provides concentration-fluctuation and/or system consumption responsive adjustments that are not contingent on conventional WTA residual level determinations, and in broad embodiments are not even dependent upon the use of a traced WTA feed.

For the purposes of the present invention, a suitable in-system concentration indicator, for a given WTA, is one that has a fluorescence characteristic which is proportional to, inversely proportional to, or convertible in some respect to, the in-system concentration for the treatment agent. A WTA interacts with a reagent (initial or incipient reagent) to form the in-system WTA concentration indicator. The WTA, in combination with the incipient reagent, forms an in-system WTA concentration indicator that possesses the fluorescence characteristics being monitored by the fluorescence analysis technique selected, or the fluorescence analysis technique is selected based on its suitability for the in-system WTA concentration indicator.

Substances that exhibit fluorescence characteristics are referred to as fluorophores. Fluorophores are generally aromatic organic compounds and/or complexes. Many inorganic compounds and ions themselves possess no fluorescence properties. Many organic materials are nonfluorescent or have such low fluorescence intensities that they cannot be quantified by fluorescence analysis when present at low water-treatment concentrations. Materials that are either nonfluorescent or have such low fluorescence properties that they cannot be quantified by fluorescence analysis when present at low concentrations for purposes of the present invention are considered herein substantially nonfluorescent. In combination with suitable fluorophores or fluorophore precursors, however, the concentrations of substantially nonfluorescent water treatment agents can be determined by fluorescence analysis techniques. The substantially nonfluorescent water treatment agents can be considered components of the effective or final reagent (in-system WTA concentration indicator or concentration indicator) generated by the reaction product of a given substantially nonfluorescent water treatment agent with an incipient or first reagent. The incipient reagent may or may not itself be fluorescent. The final reagent may or may not be fluorescent. (For instance, a fluorescence characteristic of the indicator may be the loss of the incipient reagent's fluorescence upon the formation of the final reagent.) If both the incipient reagent and final reagent are themselves fluorescent, then the fluorescence analysis technique, including at times the selection of excitation and/or emission wavelengths, is selected to avoid, or at least minimize, interference between residual incipient reagent and the final reagent. Examples of various combinations of substantially nonfluorescent water treatment agents and incipient reagents, and selections of suitable fluorescence analysis techniques for such in-system concentration indicators, are described in more detail below.

As general examples, substantially nonfluorescent water treatment agents that are commonly used in cooling waters and other industrial water systems, and are susceptible to quantification by at least one fluorescence analysis technique by the present method, include, without limitation, zinc, orthophosphate, condensed inorganic phosphates, phosphonates (organic phosphorus-containing compounds), molybdate, boron, non-oxidizing biocides, surfactants, alkalinity and others. As general examples, substantially nonfluorescent water treatment agents that are commonly used in boiler waters, and in other industrial water systems, and are susceptible to quantification by at least one fluorescence analysis technique by the present method, include, without limitation, neutralizing amines, oxygen scavengers, organic polymers, chelants, phosphates, sodium and others. These and other substantially nonfluorescent water treatment agents in some instances might be used individually, but commonly are used with other chemical species in a multi-chemical-species water treatment program.

The process of the present invention provides an accurate determination of the degree of any changes in the in-system concentration of the WTA, alone or in combination with its system demand, and the effect of any feed rate compensations or other in-system concentration adjustments made. This information not only permits a more accurate and efficient responsive concentration adjustment, but also provides an alert for upsets in the water system that will trigger an abnormal change in the WTA's consumption rate. The information provided by the monitoring of the WTA concentration indicator is of great importance to all system operating parameters related to the concentration of, and/or system consumption for, the WTA.

The industrial water systems for which the present invention may be used are water systems of any industry which employ at least one WTA, including without limitation temperature-conditioning water systems (wherein the waters are being used as a heat and/or energy transfer media), water systems wherein a raw water stream and/or water for makeup use is being purified, a water system wherein waste materials and/or waste waters are being purified, a water system wherein solids (suspended and/or solutes) are being separated from liquids (for instance the water system of membrane-separation processes), water systems of manufacturing processes, particularly chemical industry manufacturing processes, including without limitation the processes of the pulping and papermaking industries, the steel industry, the metal working industries, the food processing industries, the mining industries, the automotive industry, the textile industry, utilities, chemical processing industries, manufacturing industries, spray paint industries, refining industries such as the refining of aluminate, and the like.

Industrial water systems are often fluid systems that contain at least about 60 weight percent water, the remainder being solids (suspended and/or dissolved) and/or nonaqueous fluids, and which commonly are flowing rather than static. In preferred embodiment the industrial water system of the present invention is an industrial system that contains at least about 65 or 70 weight percent water, the remainder being solids (suspended and/or dissolved) and/or nonaqueous fluids, and preferably which is flowing rather than static.

The present invention in broad embodiment, however, is not limited to industrial water systems, and instead may be applicable to nonaqueous fluid systems. There are instances of the use of water treatment agents in substantially nonaqueous fluid systems. For instance, neutralizing amines are used in some hydrocarbon streams in the oil refining industry. It may be highly beneficial to monitor the concentration of neutralizing amines and/or other water treatment agents in such hydrocarbon streams for the purpose of the present invention, i.e., regulating treatment agent dosage. The process of the present invention may be employed for mixed aqueous/nonaqueous fluid systems and nonaqueous fluid systems in the same manner as in aqueous systems, provided any potential interference with the fluorescence analysis arising from the nonaqueous portion of the fluid can be avoided. Since the present invention is believed to be most readily and commonly adaptable to water systems, for simplicity but not for limitation purposes the invention is described herein in terms of water systems.

Some water systems employ a plurality of water treatment agents for which the computation of accurate in-system concentrations alone, or in combination with system demands and/or system consumptions, would improve system efficiency. Such concentrations and/or system demands and/or system consumptions for the plurality of water treatment agents may be determined by quantifying a plurality of WTA indicators, each of which may be related to different water treatment agents in known proportion to their in-system concentration.

A single WTA may be subject to a plurality of system consumption conditions, and the system consumption determination of the present invention is the net system consumption for the WTA at the sampling site. Any site-specific variation in net system consumption may be determined by quantifying the WTA at a plurality of sites using the same or different WTA-concentration indicator. In more detail, some water systems may have a plurality of zones in each of which a single WTA may encounter distinct zone-specific system consumption. Such zones may be disposed sequentially or in parallel, or the water system may have a plurality of streams that each feeds to a zone or away from a zone. The present invention can be employed in any of these situations or combinations of situations, provided that the WTA concentration indicator and inert tracer are monitored in each water system zone for which a separate system consumption is to be determined.

The solids and/or solutes within the waters of these water systems may be substantially or mainly organic, or substantially or mainly inorganic, or a mixture of both organic and inorganic materials. The process of the present invention would generally not be applicable to an industrial water system wherein the water system has a high solids loading, for instance a solids loading in excess of 40%.

A water system may contain dissolved solids or dissolved gases, or it may be a slurry (dilute or concentrated), or it may be a slurry containing dissolved solids and/or gases. A water system may also contain liquids other than water, which liquids may be miscible or immiscible with water.

The commonly-encountered WTA's of cooling water systems and boiler water systems are mentioned in brief above, and cooling water systems and boiler water systems are preferred for the use of the present invention. They are highly dynamic water systems that have significant need for the advantages of the present invention. The present invention is, however, applicable to a wide variety of industrial water systems as noted above. Some characteristics of several of these water systems are described in more detail below, and such discussion is exemplary, not meant to be limiting.

COOLING WATER SYSTEMS

The high heat capacity of water makes water a favored heat transfer medium for cooling a product or process, such as those of a wide variety of industries, including the utility industries. The basic cooling system designs are once-through systems, closed recirculating systems (nonevaporative), and open recirculating systems (evaporative). Many cooling towers recirculate water, and often release heat transferred to its water through evaporation, and thereby reduce the water withdrawn from, and discharged to, natural water sources. While such modern cooling system designs benefit environmental and conservation interests, they spawn water chemistry problems within the cooling system by increasing the potential for corrosion, scaling, fouling and other deposition.

Cooling water usually does not contact the heat source directly. The cooling water and the product/process being cooled are usually both fluids, separated by a barrier that is a good heat conductor, which commonly is a metal or metal alloy. The barrier is called a heat transfer surface, and an assembly of barriers in a containment vessel is called a heat exchanger.

In cooling water systems, and most other industrial water systems, corrosion can cause premature metal failures. Deposits of corrosion products reduce both heat transfer and flow rates and reduce integrity of heat-exchange surfaces and system equipment. Scale is caused by the precipitation of compounds that become insoluble as temperature measures or decreases (e.g., $CaCO_3$ is less soluble at elevated temperature and $SiO_2$ at lower temperature) or conditions change (e.g., pH, alkalinity). Scale and deposits interfere with heat transfer and reduce flow. Fouling results from the settling out of suspended solids, build up of corrosion products, and growth of microbial masses. Fouling not only interferes with heat transfer and fluid flow, but also promotes severe corrosion under deposits.

Cooling waters, while containing generally a far lower concentration of components than for instance process fluids, nonetheless can vary widely as to their makeup. The source of the fluid, the treatment programs employed and the concentration ratio of the fluid in the system are major factors determining the type of components and the concentration thereof. Among the solutes that are present in cooling water as taken from its source are calcium ions, magnesium ions, sulfate ions, silicate ions, alkalinity and suspended substantially inorganic solids. Among the solutes that may be introduced into cooling water in water-treatment programs are zinc, molybdates, silicates, polyphosphates, polyol esters, phosphonates, alkalinity, natural organics, synthetic organic polymers, nonoxidizing biocides, halogen-based biocides and ozone. Cooling waters generally can be characterized as normally having a pH of from about 6.5 to about 9.5, having a concentration of solutes of up to about 10,000 ppm, and having a concentration of suspended, or colloidal, solids of not more than up to about 200 ppm.

BOILER WATER SYSTEMS

A boiler is a vessel in which water is vaporized into steam by the application of heat, typically on a continuous basis. The steam generated is most often used either as a direct or indirect heat transfer medium and/or to generate electric power. High pressure and/or high capacity boilers generally are water-tube boilers in which water is circulated within tubes and the applied heat (combustion products such as flame and hot combustion gases) flows across the outside of the tubes. Some of these water tubes may comprise the walls of the furnace in which the heat-generating combustion occurs.

Boiler water systems include the water systems of recovery boilers, used for instance in the pulp and paper industry, power boilers, boilers in the chemical process industry and the nuclear power generation industry which may contain fluids with a high radioactive contamination level under high pressure.

Limits on boiler cycles of concentration, so as to limit the maximum impurity concentration within a boiler, are routinely set by boiler and turbine manufacturers, water treatment companies and the industrial plants employing the boilers. Boiler feedwater, which normally is comprised of both makeup water and recirculated condensate water, contains some impurities regardless of the extent to which such waters are treated before being fed to a boiler. When steam is generated, substantially pure $H_2O$ vapor is discharged from the boiler, leaving the impurities (the dissolved and suspended solids) behind, which increases their concentration in the boiler water. The discharged steam is replaced by contaminant-containing feedwater. An ever increasing concentration of dissolved and suspended solids in the boiler water would inevitably result in very serious problems, including deposit formation, corrosion, foaming and carryover, decreased heat transfer efficiency, boiler tube failure or occlusion, and the like. Boiler-impurities concentration (boiler solids concentration) is offset by withdrawing water as normal blowdown and replacing that blowdown with makeup water containing a lower concentration of dissolved and suspended solids. The heat energy in the normal blowdown, however, is a major factor reducing a boiler's thermal efficiency, and therefore a blowdown rate in excess of that required to limit solids concentration is routinely avoided. An excessive blowdown rate also unnecessarily increases water costs.

Intermediate and high pressure boilers have heat transfer rates in excess of 100,000 $Btu/ft^2$-hr and the presence of an even extremely thin deposit layer within the boiler would cause a serious elevation in the temperature of the tube metal. Therefore the feedwater purity is very high and the permitted concentration of impurities introduced with the feedwater is very low. These are almost invariably high cycles value boilers with almost constant steam generation demands.

Both the limitations on boiler concentration cycles and the employment of boiler water treatment programs are intended for, and are generally necessary to, the avoidance of serious scale formation/deposition despite an otherwise adequate feed water purification program.

WASTE WATER SYSTEMS

The ultimate fractions produced in a typical waste water system are destined either for recycle to the water system generating the waste, or for recycle to a different system, or for disposal. These "products" of a waste water treatment plant seldom have a value commensurate with that of the water system generating the waste. A typical waste water treatment plant is therefore extremely sensitive to the economics of the treatment agent involved, and unlike the average temperature-conditioning water system, its influent is extremely variable and its WTA feed and regulating means are far less sensitive than that of a typical cooling water plant. The process of the present invention enables a plant to be proactive in its WTA in-system concentration adjustments, and abnormally low WTA in-system concentration determinations will alert plant operators of inlet water quality upsets. Waste waters and/or systems for purposes of the present invention are most often waters that have been discharged from a prior system or cooling water system or boiler stream.

RAW WATER SYSTEMS

Raw water streams and/or systems for the purposes of the present invention are waters being prepared for addition to, and use in, a water system such as a cooling water system or boiler stream, and include without limitation well water, river water and other surface water supplies.

MEMBRANE FILTRATION WATER SYSTEMS

The use of semipermeable membranes is a comparatively recent addition to the technology of industrial water renovation or purification. In membrane separation, influent passes though the membrane as a result of a driving force, or a combination of driving forces, leaving behind some portion of its original impurities as a concentrate. Membrane filtration is a membrane separation process that removes not only suspended particles, but also colloids and solutes from feedwater, as described in more detail below.

The problems that have historically plagued industrial applications of membrane separation include membrane scaling, membrane fouling and membrane degradation. These problems previously kept membrane separation costs relatively high and limited its use to special situations, for instance situations in which the removed impurities themselves were of commercial value. Improvements in membranes and application technology have now made membrane separation a more commercially-practical technology for purifying raw water for industrial water systems, industrial-process effluent treatment, treatment of other waste water, desalination of brackish water, sea water, nonaqueous fluids, mixtures of aqueous and nonaqueous fluids and the like. Membrane separation has also been made more practical for industrial use, particularly industrial use for raw and wastewater purification, by improved tools for determining membrane performance, including detection and/or quantification of membrane fouling, and the dosage and/or performance of membrane-filtration chemicals. Membrane separation would be made still more practical for industrial use by even better diagnostic tools.

Diagnostic monitoring of membrane filtration systems is extremely important to operational efficiency and to avoid foreshortening the useful life of the membrane. These diagnostic monitorings are routinely made in some manner in industrial membrane filtration plants because the diagnostic information provided is now understood and accepted as essential to the system's practicality for industrial use. Monitorings of membrane-filtration chemicals (WTA's including without limitation treatment chemicals that enhance membrane-separation process performance, antiscalants that retard/prevent membrane scale deposition, antifoulants that retard/prevent membrane fouling, biodispersants, microbial-growth inhibiting agents such as biocides and cleaning chemicals that remove membrane deposits) to determine actual feed rates and in-system concentrations would greatly enhance the operational efficiency of the system and protect the membrane, but conventional techniques either so lack sensitivity or take so long that expeditious responsive action is not always possible. Moreover, these plurality of monitorings routinely require the employment of a plurality of analytical techniques, which situation complicates and increases the expense of the indispensable diagnostic programs.

The present invention is of course not limited to temperature-conditioning water systems or water-purification water systems. The present invention may be applied to monitor the in-system concentration of, or system demand upon, a downhole corrosion inhibitor in the oil and gas well industry. The present invention may be applied to monitor the in-system concentration of, or system consumption upon, water treatment agents employed in ore beneficiation water systems. The present invention may be applied to monitor the in-system concentration of, or system consumption upon, water treatment agents employed in chemical refining water systems.

The water of typical water system can be characterized by the following physical and/or chemical property ranges, although the present invention is not limited to water systems within such ranges:

a pH of from about 2 to about 12;
a temperature of from about 41° F. to about 650° F.;
an insoluble solids content of from about 0.1 ppm to about 1,000 ppm; and
a total solids content of from about 10 ppm to about 100,000 ppm.

WATER SYSTEMS OF OIL, GAS AND GEOTHERMAL WELLS

Many oil, gas and geothermal wells employ extensive water systems in contact with metal surfaces. Such metal surfaces, particularly those disposed downhole, have severe potential water chemistry problems, including without limitation potential corrosion and scaling problems. Water treatment programs employed to resist these problems would be greatly enhanced by a sensitive method for monitoring real-time in-system concentration of, or system consumption of, the water treatment agents used therein.

An important advantage of the present invention is that by monitoring a WTA-concentration indicator, rather than the treatment agent itself, the monitoring can be achieved by a fluorescence analysis despite the WTA being a substantially nonfluorescent specie. Moreover, the present invention is also useful for those WTA's that are themselves sufficiently fluorescence for fluorescence analysis, but a direct fluorescence analysis of the water sample is thwarted by the fluorescence interference within a given water system. In such instances, the WTA would have a system-specific substantially-nonfluorescent property.

In preferred embodiments, the zero-consumption concentration of at least one water treatment agent is also monitored, more preferably by fluorescence analysis, for instance by using a "traced treatment agent", such as a treatment agent product or makeup water to which an inert fluorescence tracer has been added in known proportion to the water treatment agent. Monitoring the level of such tracer within the system determines the zero-consumption concentration of the treatment agent in the system. The concentration of an inert tracer added to the system in proportion to a treatment agent is proportional to the theoretical concentration of the treatment agent in the absence of any treatment-agent selective impacts on concentration. Most any water treatment agents will undergo some type of consumption within the system that is selective to it, that is by virtue of a mechanism that changes the concentration of the treatment agent but has no impact on the concentration of an inert tracer. The actual concentration of a water treatment agent in a water system at any point in time is a function of the amount being added per time unit and the amounts selectively and unselectively consumed (lost) per time unit. When the in-system concentrations of both a water treatment agent and an associated inert tracer are known, system consumption for the WTA can be determined.

The concentration of an inert tracer added to the system in proportion to a treatment agent is also a measure of the impact of any adjustments of system controls to regulate the in-system concentration of a treatment agent, particularly when a plurality of adjustments are made concomitantly. For instance, if the goal is a 20 percent (or less) decrease in the concentration of the treatment agent then in the system, and the chosen control adjustment is a temporary increase the blowdown from the system with a concomitant fresh water replacement and treatment agent feed, the inert tracer monitoring will disclose when the goal has been met as to the dilution mechanism, but of course not as to any treatment-agent selective impacts on its concentration during the time interval. The greater the complexity of the nonselective influences on in-system concentration, the more useful is the use of an inert tracer to track the net effect of these influences. Nonetheless the complimentary monitoring of an inert tracer may be extremely advantageous even when relatively simple control adjustments are made or when quantitative data is not determined. For instance, when the WTA indicator monitoring indicates that an increase in treatment agent in-system concentration is needed, a monitoring of a tracer in the system may be used to confirm that an upward adjustment of zero-consumption in-system concentration of the treatment agent has been made, without quantifying the in-system concentration of the treatment agent before and/or after the adjustment.

A "feed rate" monitoring for the inert tracer of a traced water treatment product or makeup water is at times a preferred additional procedure, for instance by monitoring the tracer's concentration in a feed line upstream of the point at which the product and/or water is delivered to the system. Such "feed rate" monitoring is used to more precisely determine the actual amount of treatment agent being added to the system when the tracer is monitored in the feed line. The regulating of the in-system concentration of the present invention might combine at least some of the information provided by the monitoring of a tracer(s) upstream or downstream of the feed inlet to the water system with at least some of the information available concerning the concentration of the tracer(s) in the water treatment agent feed.

The regulating of a water treatment agent in-system concentration may include any of a number of determinations based on monitoring of one or more inert tracers, which values may be relative values, substantially quantitative values, or approximate quantitative values. The proportion between a tracer and the active water treatment agent as fed to a water system need not be known provided the proportion is constant, or instead the proportion can change provided sufficient information is available to correlate the monitorings over the desired time period.

To quantify the fluorescent characteristic of an in-system WTA concentration indicator, a variety of fluorescence analysis methods are available for use singly or in combination. Such fluorescence analysis techniques include, without limitation, techniques that measure and/or indicate:

I. the appearance or disappearance of fluorescence;
II. a shift in excitation and/or emission wavelengths of fluorescence;
III. a fluorescence quenching or elimination of quenching (by a specific substance);
IV. fluorescence changes based on specific light absorbance changes (increase or decrease);

V. a well-defined temperature-dependency of fluorescence;
VI. a well-defined pH-dependency or other water condition dependency of fluorescence; and
VII. at times the exploitation of a temperature-dependency and/or pH-dependency of fluorescence to see the effects of techniques 1 to 4 above.

FLUORESCENCE EMISSION SPECTROSCOPY

The detection and quantification of specific substances by fluorescence emission spectroscopy are founded upon the proportionality between the amount of emitted light and the amount of a fluorescent substance present. When energy in the form of light, including ultra violet and visible light, is directed into a sample cell, fluorescent substances therein will absorb the energy and then emit that energy as light having a longer wavelength than the absorbed light. A fluorescing molecule absorbs a photon resulting in the promotion of an electron from the ground energy state to an excited state. When the electron's excited state relaxes from a higher energy vibrationally-excited state to the lowest energy vibrationally-excited state, energy is lost in the form of heat. When the electron relaxes to the ground electronic state, light is emitted at a lower energy than that absorbed due to the heat-energy loss, and hence at a longer wavelength than the absorption. The amount of emitted light is determined by a photodetector. In practice, the light is directed into the sample cell through an optical light filter so that the light transmitted is of a known wavelength, which is referred to as the excitation wavelength and generally reported in nanometers ("nm"). The sample cell is designed to optimize the fluorescence response for the analyte, depending on the analysis method chosen. The emitted light is similarly screened through a filter so that the amount of emitted light is measured at a known wavelength or a spectrum of wavelengths, which is referred to as the emission wavelength and generally also reported in nanometers. When the measurement of the fluorescence intensity of specific substances or categories of substances at low concentrations is desired or required, such as often is the case for the process of the present invention, the filters are set for a specific combination of excitation and emission wavelengths, selected for substantially optimum low-level measurements.

In general, the concentration of an in-system WTA concentration indicator, or fluorescent associated inert tracer (fluorescent WTA-feed tracer), can be determined from a comparison of a sample's emissions intensity to a calibration curve of the given in-system WTA concentration indicator's or tracer's concentration versus emissions, for the same set of excitation wavelength/emission wavelengths. Such a concentration-by-comparison method by which the sensed emissions are converted to a concentration equivalent preferably is employed to determine concentrations of a concentration indicator (and in turn the in-system WTA concentration) or tracer that are within the concentration range over which a linear emission response is observed, and this concentration range is referred to herein as the "linear-emission-response concentration range". The linear-emission-response concentration range is to some extent dependent upon the specific in-system WTA concentration indicator or tracer and the excitation wavelength/emission wavelength set employed. At in-system WTA concentration indicator or tracer concentrations higher than a given in-system WTA concentration indicator's or tracer's linear-emission-response concentration range, there is a negative deviation from ideal (linear) behavior, the degree of emission for a given concentration being less than predicted by a linear extrapolation. In such instances, the sample can be diluted by known factors until the concentration of the in-system WTA concentration indicator or tracer therein falls within the linear-emission-response concentration range. Two other correction techniques are available when the concentration is higher than the linear-emission-response concentration range. Since the linear-emission-response concentration range is to some extent dependent upon the excitation wavelength/emission wavelength set employed, an alternate excitation wavelength/emission wavelength set could be used. The use of sample cells with shorter pathlengths for the excitation/emission light will also correct or alleviate the problem. If the in-system WTA concentration indicator or tracer is present in the sample at only exceptionally low concentrations, there are techniques for concentrating the in-system WTA concentration indicator or tracer by known factors until its concentration falls within the linear-emission-response concentration range or is otherwise more readily measured, for instance by liquid-liquid extraction. Nonetheless, preferably a calibration curve over the linear-emission-response concentration range would be prepared or obtained before employing a given in-system WTA concentration indicator or tracer. Preferably the in-system WTA concentration indicator or tracer would be respectively selected or added to the WTA feed in an amount sufficient to provide a concentration of the in-system WTA concentration indicator or tracer in the sample that is within the linear-emission-response concentration range. Generally, the linear-emission-response concentration range of an in-system WTA concentration indicator or tracer is sufficiently broad to readily determine the amount of the in-system WTA concentration indicator or tracer that will be sufficient for this purpose. A linear-emission-response concentration range for an unmodified sample and typical standard equipment will most often extend through a concentration range from a concentration of "m" to a concentration of at least 2,000 m. When "extended" operation techniques are employed, for instance sample dilution, use of an optimal alternate excitation wavelength/emission wavelength set, and/or use of optimal same cell pathlengths, a linear-emission-response concentration range can be extended from m to 10,000,000 m and beyond.

A determination of the concentration of an in-system WTA concentration indicator or fluorescent tracer in a system can be made when the concentration of the in-system WTA concentration indicator or tracer in the water system is only several parts per million (ppm) or even parts per billion (ppb) for some of the in-system WTA concentration indicators or tracers that can be employed in the process of the present invention. In preferred embodiment, the amount of an in-system WTA concentration indicator in the system or tracer added to the WTA feed should be sufficient to provide a concentration of the in-system WTA concentration indicator or tracer in the water system sample of from about 1 ppb to about 10 ppm. Such analyses (the measurements of the light emitted in response to the light transmitted to the water system sample) can be made on-site, preferably on an almost instant and continuous basis, with simple portable equipment.

As mentioned above, at times it may be desired to employ a plurality of in-system concentration indicators or tracers. For instance, it may be desired to monitor more than one WTA, and a separate in-system WTA concentration indicator or tracer may be used for each monitored WTA, and thus the separate in-system concentrations for more than one WTA would be determined by the process of the present invention. In other instances it may be desired to use a plurality of in-system WTA concentration indicators or tracers solely for the regulation of a single WTA, for instance to confirm the data provided by an in-system WTA concentration indicator or tracer. Such separate and distinct in-system concentration indicators or tracers can all be detected and quantified in a single water system sample despite all being fluorescent substances if their respective wavelengths of emission do not interfere with one another. Thus concurrent analyses for multiple in-system concentration indicators or tracers are possible by selection of in-system concentration indicators or tracers having appropriate spectral characteristics. Preferably separate wavelengths of radiation should be used to excite each of the in-system concentration indicators or tracers, and their fluorescent emissions should be observed and measured at separate emission wavelengths. A separate concentration calibration curve may be prepared or obtained for each in-system WTA concentration indicator or tracer. In other words, more than one in-system WTA concentration indicator or tracer can be employed, and then the presence and/or concentration of each such in-system WTA concentration indicator or tracer in the water system may be determined using analytical parameters (particularly the excitation/emission wavelengths) effective for each such in-system WTA concentration indicator or tracer, which analytical parameters preferably are sufficiently distinct to differentiate between measurements. Since a plurality of in-system concentration indicators or tracers may be separately but concomitantly monitored, the present invention does not exclude the use of one or more additional in-system concentration indicators or tracers for purposes other than the present invention, nor does it exclude the concomitant use of an in-system WTA concentration indicator or tracer for purposes of the present invention and for some other purpose.

Fluorescence emission spectroscopy on a substantially continuous basis, at least over a given time period, is one of the preferred analytical techniques for the process of the present invention. It is one of the preferred analysis techniques for quantifying and determining the concentration of the in-system WTA concentration indicator or tracer in a system for the purpose of monitoring the in-system WTA concentration and regulating the water treatment agent feed. Fluorescence analysis is an analytical technique having significant advantages.

A dual-monochromator spectrofluorometer can be used for a fluorometric analysis conducted on an intermittent basis and for on-line and/or continuous fluorescence monitoring. Portable or compact fluorometer equipped with appropriate excitation and emission filters and a quartz flow through cell are commercially available, for instance from Turner Designs (Sunnyvale, Calif.).

In general, for most fluorescence emission spectroscopy methods having a reasonable degree of practicality, it is preferable to perform the analysis without isolating in any manner the WTA, the concentration indicator or the WTA-feed tracer. Thus there may be a small degree of background fluorescence in the water system on which the fluorescence analysis is conducted, which background fluorescence may come from chemical compounds in the water system that are unrelated to the present invention. The analysis methods are designed so that background fluorescence is low, the relative intensities (measured against a standard fluorescent compound at a standard concentration and assigned a relative intensity, for instance a relative intensity of 100) of the fluorescence of the in-system WTA concentration indicator or tracer versus the background can be very favorable, for instance a ratio of 100/10 or 100/2 when certain combinations of excitation and emission wavelengths are employed even at low in-system WTA concentration indicator or tracer concentrations, and such ratios would be representative of relative fluorescence intensities (under like conditions) of respectively 10 and 50. In preferred embodiment, the excitation/emission wavelengths and/or the in-system WTA concentration indicator or tracer are selected to provide a relative fluorescence of at least about 5 or 10 for the given background fluorescence anticipated.

For instance, for most water system backgrounds, a relative performance of at least about 5 at a reasonable concentration is a very suitable fluorescence signal for either an in-system WTA concentration indicator or tracer. When there is or may be a specific chemical specie of reasonably high fluorescence in the background, the in-system WTA concentration indicator or tracer and/or the excitation and/or emission wavelengths often can be selected to nullify or at least minimize any interference of the tracer measurement(s) caused by the presence of such specie.

One method for the continuous on-stream monitoring of fluorescent chemicals such as an in-system WTA concentration indicator or tracer by fluorescence emission spectroscopy and other analysis methods is described in U.S. Pat. No. 4,992,380, B. E. Moriarity, J. J. Hickey, W. H. Hoy, J. E. Hoots and D. A. Johnson, issued Feb. 12, 1991, incorporated hereinto by reference.

COMBINED HPLC-FLUORESCENCE ANALYSIS

The combination of high-pressure liquid chromatography ("HPLC") and fluorescence analyses of in-system concentration indicators or tracers is a powerful tool for the present invention, particularly when very low levels of an in-system WTA concentration indicator or tracer are used or the background fluorescence encountered would otherwise interfere with the efficacy of the fluorescence analysis. The HPLC-fluorescence analysis method allows an in-system WTA concentration indicator or tracer compound to be separated from the fluid matrix and then an in-system WTA concentration indicator or tracer concentration can be measured. The combination of HPLC-fluorescence analysis is particularly effective for measuring minute levels of in-system WTA concentration indicator or tracer in highly contaminated fluids.

When the WTA indicator is nonfluorescent and the incipient reagent is fluorescent, a fluorescence analysis technique, such as those described above, will be focused on the fluorescence of the incipient reagent. The measure of the target specie will be the loss of the incipient reagent, as it is consumed in the formation of the WTA indicator, as manifested by the change of its fluorescence intensity and/or excitation/emission wavelength characteristics. When both the WTA indicator and the incipient reagent are fluorescent, and the difference is the respective wavelengths of maximum emissions, then the fluorescence analysis might focus on either the decrease in the emissions at the maximum emission wavelength of the incipient reagent, or the increase in the emissions at the maximum emission wavelength of the WTA concentration indicator as it is formed by interaction between the WTA and the incipient reagent.

While fluorescence analysis of an inert fluorescent tracer is a preferred technique when an inert tracer is being monitored, as seen from the above descriptions, other methods are available for monitoring other inert tracers, and in broad embodiment the present invention does not exclude the use of such tracers and methods.

COLORIMETRY ANALYSIS

Colorimetry or spectrophotometry may be employed to detect and/or quantify a chemical tracer. Colorimetry is a determination of a chemical specie from its ability to absorb ultraviolet or visible light. One colorimetric analysis technique is a visual comparison of a blank or standard solution (containing a known concentration of the tracer specie) with that of a sample of the fluid being monitored. Another colorimetric method is the spectrophotometric method wherein the ratio of the intensities of the incident and the transmitted beams of light are measured at a specified wavelength by means of a detector such as a photocell or photomultiplier tube. Using a colorimetric probe, a fiber optic (dual) probe, such as a Brinkman PC-80 probe (570 nm filter), a sample solution is admitted to a flowcell in which the probe is immersed. One fiber optic cable shines incident light through the sample liquid onto a mirror inside the cell and reflected light is transmitted back through the sample liquid into a fiber optic cable and then to the colorimetric analyzer unit, which contains a colorimeter, by the other cable. The colorimeter has a transducer that develops an electrical analog signal of the reflected light characteristic of the tracer concentration. The voltage emitted by the transducer activates a dial indicator and a continuous line recorder printout unit. A set point voltage monitor may be employed to constantly sense or monitor the voltage analog generated by the colorimeter, and upon detection of a tracer signal (discussed below), a responsive signal may be transmitted to a responsive treatment agent feed line to commence or alter the rate of feed. Such a colorimetric analysis technique and the equipment that may be employed therefor are described in U.S. Pat. No. 4,992,380, B. E. Moriarity, J. J. Hickey, W. H. Hoy, J. E. Hoots and D. A. Johnson, issued Feb. 12, 1991, incorporated hereinto by reference. Chemical tracers suitable for use in conjunction with a colorimetric technique include transition metals and substances which show light absorbance which is detectable from that of other species present in the system fluid or substances which react with color-forming reagents to produce light absorbance which is detectable from that of other species present in the system fluid.

ION SELECTIVE ELECTRODE ANALYSIS

An ion selective electrode may be used to determine the concentration of an inert chemical tracer through the direct potentiometric measurement of specific ionic tracers in aqueous systems. These electrodes respond only to selected ionic materials and gases dissolved in liquids, and hence such tracers must be ionized (or dissolved gases) in the environment in which they are to be determined. Ion selective electrodes work like pH electrodes, depending on a potential developed across a thin membrane by the difference in the concentrations of the ion (or gas) to be measured on each side of the ionically conducting thin layer. The concentration within the electrode is fixed and the potential varies with the concentration of ions (or gas) in the same. By calibration (the potential or current versus the concentration), the ionic (or gas) concentration at the sample electrode can be indexed to a reference or standard electrode that is insensitive to the tracer ion. To provide continuous monitoring of the tracer, the electrodes may be dipped directly into a stream of one of the fluids (collectively comprising a flow cell), or the fluid being monitored may be passed through an external flow cell into which the ion-selective and reference electrodes have been inserted. An ion selective electrode tracer monitoring technique and the equipment therefor are described in U.S. Pat. No. 4,992,380, B. E. Moriarity, J. J. Hickey, W. H. Hoy, J. E. Hoots and D. A. Johnson, issued Feb. 12, 1991, incorporated hereinto by reference.

TRANSITION METAL ANALYSIS

A transition metal compound (transition metal ions, oxy-anions, cations and associated complexes) can be quantitatively measured by one or more of known techniques. A preferred technique is the colorimetry analysis described above. Another technique is molecular absorption. Molecular absorption in the ultra violet and visible region depends on the electronic structure of the molecule. The energy absorbed elevates electrons from orbitals in a lower-energy state to orbitals in a higher-energy state. A given molecule can absorb only certain frequencies because only certain states are possible in any molecule and the energy difference between any ground and excited state must be equal to the energy added. At a frequency that is absorbed by a molecule, the intensity of the incident energy is greater than the intensity of the emergent energy, and is a measure of the absorbance. A sample of the fluid being monitored may be compared to a calibration curve (absorbance versus concentration) prepared from standard solutions containing known concentrations of the transition metal (or other suitable tracer specie) to detect and determine the concentration of the tracer. A molecular absorption technique for transition metal tracers is described in U.S. Pat. No. 4,992,380, B. E. Moriarity, J. J. Hickey, W. H. Hoy, J. E. Hoots and D. A. Johnson, issued Feb. 12, 1991, incorporated hereinto by reference.

Analytical techniques for quantifying the presence and/or concentration of a chemical specie without isolation thereof are within an evolving technology, and the above survey of reasonable analytical techniques for use in monitoring an in-system WTA concentration indicator or tracer in the process of the present invention may presently not even be exhaustive, and most likely techniques equivalent to the above for the purposes of the present invention will be developed in the future.

Chemical compound(s) selected as an inert WTA feed tracer should be soluble or dispersible in the water system in which it is formed or to which it is added and should be either stable in the environment thereof for the useful life expected of the inert tracer, or its loss from the water system due to degradation, deposition, complexation, or other phenomena should be predictable and compensative, particularly since it is desired not merely to detect the presence of some amount of the inert tracer, but also to determine its concentration and correlate its concentration to the feed rate of the WTA.

In preferred embodiment, the combination selected as the in-system WTA concentration indicator and/or WTA-feed tracer and the analytical technique(s) selected for measuring such concentration indicator and/or tracer, should permit such determination(s) without isolation of the concentration indicator and/or tracer, and more preferably should permit such measurement(s) on a continuous and/or on-line basis.

WATER TREATMENT AGENT APPLICATIONS

WTA's are routinely employed in water systems to diminish or reduce corrosion, formation of scale and other deposits, growth of microorganisms, and other undesirable effects arising most often from unavoidable impurities in the water supply.

Corrosion of processed metals, such as steel, copper, and zinc, is a process whereby elemental metals, in the presence of water and often but not always oxygen, are converted to oxides. Although corrosion is a complicated process, it may be considered an electrochemical reaction involving three steps which occur at the anodic and cathodic sites of a metal surface, as follows:

1. Loss of metal to the water solution in oxidized cationic form at an anodic site, with concomitant release of electrons ("anodic reaction");
2. The flow of the released electrons to a cathodic site; and
3. Oxygen at a cathodic site uses the electrons to form hydroxyl ions ("cathodic" reaction), which flow to an anodic site. The alternative cathodic reaction in the absence of oxygen is the formation of hydrogen atoms which may then form $H_2$ gas (3 Fe+4 $H_2O \rightarrow Fe_3O_4 + 4H_2$).

These three basic steps are necessary for corrosion to proceed, and the slowest of the three steps determines the rate of the overall corrosion process. The cathodic reaction is often the slowest of the three steps because the diffusion rate of oxygen through water is slow. A corrosion control program usually depends on specific inhibitors to stop the anodic reaction or slow the cathodic reaction, or both. Among the various types of corrosion inhibitors are inorganic and organic compounds, which act by adsorbing or chemisorbing as thin layers on metal surfaces to separate the water and metal. These materials form and maintain a dynamic barrier between the water and metal phases to prevent corrosion. Typical WTA's employed frequently as corrosion inhibitors to stop/reduce the anodic/cathodic reactions include without limitation chromates, orthophosphate, nitrite, silicate, carbonates, polyphosphate, zinc, molybdates, organic filming amines, and phosphonates. Oxygen scavengers such as sodium bisulfite, ammonium bisulfite, sodium sulfite, erythorbic acid, hydrazine, carbohydrazine and others are also frequently employed as WTA's to reduce corrosion in boiler water systems, oil field water systems and others.

Mineral scales are hard crystalline deposits that adhere to surfaces. The major sealants are: $CaCO_3$, $CaSO_4$, $BaSO_4$, $SrSO_4$ and others. ($Fe_2O_3$ and $SiO_2$ are generally considered foulants, not scalants.) Mineral scale deposits are normally formed from dissolved solids precipitated from the water that have concentrated on a surface in contact with the water, such as the membrane of a membrane filtration system. Antiscalants presently used in membrane filtration systems and other industrial water systems include polymers, fed in aqueous solution, which inhibit the formation and growth of alkaline earth carbonate and sulfate scales (i.e., $CaCO_3$, $CaSO_4$). Some polymeric antiscalants modify the crystalline structure of the scale-forming minerals, preventing scale from adhering well to the surface(s) of the water system and thus promoting their removal with the systems effluent. Polymeric antiscalants in some water systems, for instance boilers, chelate hardness ions and prevent precipitation of the minerals entirely. Chelating polymeric antiscalants include polyacrylic acid which, in ionized form, can chelate calcium cations. The use of an effective antiscalant can minimize or eliminate the need for acid feed which is used in some systems for scale control, help suspend solids and colloids in solution, and inhibit the precipitation of $CaCO_3$ and $CaSO_4$. Typical WTA's employed frequently as antiscalants include limitation polyphosphates, polyol esters, phosphonates, all-organics, synthetic polymers (often anionic polymers), and nonpolymeric chelating agents such as ethylenediaminetetraacetic acid (EDTA),.

Boric acid is used as an agent that inhibits the formation of amorphous silica scale in industrial water systems. The use of boric acid its water-soluble salts and/or another boron compound that forms orthoborate ion when dissolved in or hydrolyzed by water, alone or as an admixture with a water-soluble polypolar organic compound containing hydroxyl, primary amino, or secondary amino functional groups (molecular weight not exceeding 500), as an inhibitor of amorphous silica scale formation on surfaces in contact with industrial waters, is taught in U.S. Pat. No. 4,532,047, issued on Jul. 30, 1985, inventor Leonard Dubin, incorporated hereinto by reference, and U.S. Pat. No. 4,584,104, issued Apr. 22, 1986, inventor Leonard Dubin, incorporated hereinto by reference. Boric acid also has other industrial applications. It is a buffer and has bacteriostatic and fungicidal properties.

Foulants are soft, noncrystalline deposits that adhere to the surfaces in contact with the water of a water system. Typical foulants are deposits from and/or of suspended solids, colloidal materials, oils, metal oxides, silicas and biological growth (microorganisms). Foulants are normally formed from suspended matter carried in an aqueous influent. The formation of foulant deposits are conventionally combated by filtration ahead of the membrane, chemical treatment of the water (particularly influent water), monitoring to determine the composition and/or source of foulants and potential foulants (water and filter analysis), and periodic system maintenance (cleaning). Chemical treatments applied to the fresh influent fluid as a pretreatment to properly condition it may include coagulants, flocculants and/or pH adjustments to prevent precipitation. Biocides may be added to fresh influent and/or recycled fluid to prevent the growth of microbes. Prefilters can help reduce foulants to some extent by removing large suspended solids (>2 microns). Typical WTA's employed frequently as antifoulants include without limitation all-organics, natural organics, synthetic polymers (often anionic polymers), and nonoxidizing biocides.

Surfaces in contact with the water of industrial water systems are often prone to fouling by accumulation of microorganisms. This fouling is at times referred to as microbial deposition, biofouling or sliming. Typical WTA's employed frequently as antimicrobial agents include without limitation nonoxidizing biocides and oxidizing biocides such as chlorine/bromine and ozone.

The addition of a dispersant to an industrial water system is a common factor in many water system treatment programs. A dispersant might reduce the total amount of other WTA's needed to control deposition on surfaces, prolong the effectiveness of other WTA's and/or enhance the overall control, in contrast to an equivalent process without a dispersant. The dispersant used in some systems is a nonionic surfactant, such as an ethylene oxide/propylene oxide block copolymer nonionic surfactant. When the surface being protected by the process of the present invention is a papermachine surface, the optional inclusion of a dispersant in the papermaking water is preferably the inclusion of a nonionic surfactant. Another type of frequently used dispersant is a polyelectrolyte, particularly an anionic water-soluble, polymer having a weight-average molecular weight within the range of from about 500 or 1,000 to about 100,000. The type of anionic dispersing agent employed in many water systems has a sufficient anionic charge density, when ionized to negatively charged species, so as to effectively provide particle dispersion or threshold inhibition activity in the aqueous system to which they are added. An anionic dispersing agent polymer often contains sites which can ionize to the carboxylate anion ($-COO-$), the sulfonate anion ($-SO_3-$), or combinations of such anionic sites. Such polymer(s) frequently have an anionic charge density of at least about 10 mole percent, and commonly at least about 20, or 25, mole percent of mer units containing at least one such anionic site, such mer units being a segment of the polymer(s) containing two backbone carbons. The polymeric anionic dispersant may have mer units other than anionic mer units, such as (meth)acrylamide mer units and (meth)acrylamide mer units containing lower alkyl substituents to the amide nitrogen, such as t-butyl (meth)acrylamide and other mer units that may be incorporated into the polymeric anionic dispersant without undue loss of the required dispersion activity and water solubility. A dispersing agent may also be an anionic polymer together with one or more organo phosphonates.

DEFINITION OF A WATER TREATMENT AGENT

As indicated from the list of WTA's above, numerous chemical species are employed in one or more capacities as water treatment agents for one or more types of industrial water systems. Some chemical species, for instance calcium carbonate, may be a water contaminant in one industrial water system and a water treatment agent added to another industrial water system. Not only is the above list of WTA's less than presently exhaustive, it may well become more so as time passes, as new water treatment programs with different water treatment agents are developed. A water treatment agent nonetheless can be, and herein is, defined as a chemical that has a role in at least diminishing a deleterious effect arising from the presence of one or more impurities in the system. A water treatment agent is normally intentionally added to and/or maintained in the system. Frequently, but not always, it is desirable to maintain a residual concentration level of a water treatment agent in a given system. Frequently, but not always, it is desirable to maintain a target or optimal residual concentration level of a water treatment agent in a given system. A water treatment agent may have a explicit counteractive activity against a specific category of impurities. For instance, some corrosion inhibitors counteract corrosion arising from the presence of corrodents generally in a system. A water treatment agent may have a selective counteractive activity against one or more impurities within a category of impurities. For instance, some corrosion inhibitors counteract corrosion arising from the presence of one or more specific corrodent species in a system. A water treatment agent may have a counteractive activity against the harmful effects of impurities in and of itself, or have such a counteractive activity, or an enhanced counteractive activity, in combination with one or more other water treatment agents. A water treatment agent may be maintained in a system as a prophylactic measure despite the absence of detectable level of its target impurity, that is the impurity against which it has a counteractive activity. A water treatment agent is generally water soluble at least at the concentration level at which it is maintained in a system.

Many categories of water treatment agents, impurities and deleterious effects arising from the presence of impurities are described and/or enumerated herein, but these descriptions and/or enumerations are not believed exhaustive either as to the categories or the individual species within the categories. Instead these descriptions and/or enumerations are exemplitive, and it is believed that a person of ordinary skill in the art is able to readily determine whether a chemical specie is a water treatment agent for a given system or not.

The in-system concentration of a water treatment agent determined by the present invention is generally the residual concentration of the water treatment agent in solute form in a system. The water treatment agent for which the in-system concentration is determined by the present process is preferably a water soluble water treatment agent. The water treatment agent for which the in-system concentration is determined by the present process is preferably one that has an established target and/or optimal residual concentration for the given system or given category of system. The water treatment agent for which the in-system concentration is determined by the present process is preferably one that is homogeneously distributed in the fluid of the system, instead of being present at different concentrations in different portions of the fluid.

INORGANIC WATER TREATMENT AGENT IONS

Chemical species such as zinc, molybdate, silica, boron, aluminum, phosphate and other species are (or can be) inorganic WTA ions. All of these ions are found as active components of some WTA programs. These ions possess no fluorescence characteristics. Nonetheless all are susceptible to quantification by fluorescence analysis by reaction/interaction with an incipient reagent to form an in-system WTA concentration indicator. Conventional methods for quantifying soluble zinc, molybdate, silica, phosphate and at times other inorganic ions include atomic absorption spectroscopy (AA), inductively-coupled atomic plasma (ICAP) spectroscopy and/or manual colorimetric methods. AA and ICAP require sophisticated and expensive equipment, a very specialized sampling technique, and in some cases, a time consuming digestion procedure. AA and ICAP typically cannot be performed on-line and may require hours for the analysis completion.

Colorimetric analysis techniques are known for all of the above-noted inorganic species. Such colorimetric analysis techniques are based upon the development of a color the intensity of which can be correlated to the concentration of the subject specie. The color can take a significant amount of time to develop, delaying the measurement of the sample's absorbance and thus delaying the analytical result. A long time consumption tends to preclude continuous monitoring readings by straight forward equipment designs. As mentioned elsewhere herein, colorimetric analyses also suffer interferences from other colored species in the sample as well as sample turbidity.

THE FORMATION OF IN-SYSTEM CONCENTRATION INDICATORS

In-system WTA concentration indicators are formed by the interaction between a water treatment agent and an incipient reagent. The incipient reagent might or might not itself be fluorescent. The in-system WTA concentration indicator formed may be an adduct or a complex or other interaction product (outside of covalent-bonding interaction) in which the WTA is associated with the incipient reagent, for instance by ionic bonding. It is important to note that two or more non-fluorescent molecules may react chemically to produce a fluorophore. Alternately, the incipient reagent may react chemically with the WTA to form a fluorescent WTA concentration indicator. The interaction between the WTA and the incipient reagent produces, quenches or otherwise alters fluorescence characteristic(s) of the incipient reagent. The measurement of some fluorescence characteristic of the in-system WTA concentration indicator formed provides a value that can be correlated to the concentration of the WTA in the water system.

The medium for the formation of the in-system WTA concentration indicator and/or the fluorescence analysis of the in-system WTA concentration indicator might be a substantially aqueous medium, a mixed aqueous/nonaqueous medium or substantially nonaqueous medium. The medium for the formation of the in-system WTA concentration indicator and/or the fluorescence analysis of the in-system WTA concentration indicator might contain one or more chemical species that enhance or promote the formation of the in-system WTA concentration indicator and/or the fluorescence analysis of the in-system WTA concentration indicator. Some of the fluorescence analysis techniques are sensitive to the pH or other condition of the medium in which the in-system WTA concentration indicator is undergoing fluorescence analysis.

The addition of an incipient reagent to the water system itself is generally impractical and unnecessary. The water samples taken from the water system routinely would represent only a minute fraction of the total volume, and thus the amount of incipient reagent used is minimized. Seldom would it be desirable to contaminate the entirety of a water system with a substance that is normally foreign thereto. The present invention does not, however, exclude the use of an incipient reagent, or a precursor thereto, present in the water system itself, particularly when such approach is practical and/or necessary.

The employment of a fluorescence analysis technique to measure the fluorescence of the in-system WTA concentration indicator permits the present invention to be employed on a substantially continuous basis to provide rapid determinations. The incipient reagent can be added continuously to a continuous sample stream derived directly from an on-line water system stream. The fluorescence analysis can be conducted on this sample stream a short distance downstream from the point at which the incipient reagent is introduced. In at least most instances, the in-system WTA concentration indicator is formed and measured within moments after the sample has left the water system. In many instances, the in-system WTA concentration indicator is formed and measured within 5 minutes after the sample has left the water system. In at least most instances, the in-system WTA concentration indicator is formed and measured within ten minutes after the sample has left the water system.

Suitable techniques for the conversion of a water system sample to other than a substantially aqueous sample are known, for instance liquid/liquid extraction.

Possible incipient reagents for polyionic polymers (polyelectrolytes) are ionic, and often fluorescent, dyes of opposite charge that exhibit one of several types of polyelectrolyte concentration-dependent behavior. These kinds of behaviors generally fall within one of several categories:

(A). a lessening of the intensity of fluorescence emission when measured about a given emission wavelength peak;

(B). an increasing of the intensity of fluorescence emission when measured about a given emission wavelength peak; and (C) the appearance of a new emission peak and an increasing of the intensity of fluorescence emission about the new emission wavelength peak. The type of behavior shown is dependent upon the chemical structure of the dye and/or the polyelectrolyte/dye ratio. The decrease in intensity of the fluorescence emissions at a normally peak emission wavelength (Type A behavior) can be a fluorescence quenching or an emission wavelength shift. Type C behavior includes not only an emission wavelength shifting phenomenon but also the appearance of fluorescence in a previously weak or substantially nonfluorescent chemical. Suitable dyes include without limitation Nile Blue A and pinacyanol chloride.

Techniques from various literature sources that can be adapted for the present purposes of formation of the in-system WTA concentration indicator and/or the fluorescence analysis of the in-system WTA concentration indicator are set forth below as exemplitive and not limiting.

Zinc concentrations can be determined fluorometrically based on the formation of a zinc-morin complex incipient reagent, particularly in the presence of a nonionic surfactant enhancer or promoter, for instance as described in "Enhancement of the Fluorescence of the Zinc-Morin Complex by a Nonionic Surfactant", F. H. Hernandez, J. M. Escriche, M. T. G. Andreu, Talanta, 1986, 33(6), p. 537–540, incorporated hereinto by reference. The presence of a nonionic surfactant (such as Genapol PF-20, an ethylene oxide-propylene oxide condensate) enhances the fluorescence of the zinc-morin complex about 76-fold, which makes the quantification of low levels of zinc practical. It is reported that maximum fluorescence was seen at pH 4.7 with 1.5% surfactant and 0.009% morin, using a 433 nm excitation wavelength and measuring the fluorescence emission at 503 nm. The calibration graph is linear up to about 150 ng Zn/ml (about 150 ppb), and the detection limit is about 3 ng Zn/ml (about 3 ppb).

Another incipient reagent for the fluorescent determination of divalent metal ion concentrations is (N-(4-nitrobenzofurazan)monoaza-18-crown-6), a crown ether based fluorophoric reagent, which for example is described in "A New Metal Sensitive Fluorescence Reagent", K. W. Street, Jr. and S. A. Krause, Anal. Lett., 1986, 19(7–8), p. 735–745, incorporated hereinto by reference. Metal cation complexes with reagent display enhanced fluorescence emissions. The performance of the reagent is sensitive to the solvent system employed, and nonaqueous media provide the most favorable conditions with respect to both sensitivity and complexing ability. Although the ligand possesses intrinsic acid/base sensitive fluorescence and spectroscopic properties, the metal sensitivity is not attributed to protonation-deprotonation chemistries as is the case for many of the currently available chromogenie and fluorogenic crown reagents. The sensitivity of the reagent is influenced by the anion associated with the metal and the water content of the solvent matrix.

These and other incipient reagents for which literature sources describe method of fluorescence analysis of analytes relevant to the present invention are set forth below in summary form in Table A.

TABLE A

| Analyte | Fluorescent Reagent | Reference* |
|---|---|---|
| molybdenum | thiocyanate as a rhodamine complex | 3, 1320 |
| molybdenum | carminic acid | 3, page 1330-1 |
| molybdenum | morin extract | 3, 1340-1 |
| molybdenum | thiocyanate and rhodamine B | 7, page 112 |
| molybdenum | carminic acid | 7, page 114 |
| molybdenum (VI) | bathophenanthrolinedisulfonate a.k.a. 4,7-diphenyl-1,10-phenanthroline disulfonate | 8 |
| zinc | 8-hydroxyquinoline, a.k.a. 8-quinolinol and oxine | 3, page 1053-55 |
| zinc | 2-(2-pyridyl)benzimidazole | 3, page 1059-60 |
| zinc | rhodamine B | 3, page 1060 |
| zinc | 8-(toluene-p)-sulfonamido)quinoline | 3, page 1061 |
| zinc | 8-benzenesulfonamido-quinoline | 3, page 1068 |
| zinc | carboxymethyl-8-hydroxy-quinoline | 3, page 1069 |
| zinc | dibenzothiazolylmethane, a.k.a. 2,2'-methylenebi(benzothiazolyl) | 3, page 1069-70 |
| zinc | 8-toluenesulfonylquinoline | 3, page 1075 |
| hydrazine, ammonium | o-phthalaldehyde and HS(CH$_2$)$_2$OH | 5, page 23 |

*The literature references corresponding to the numbers listed in Table I and incorporated hereinto by reference are: (3) "Photometric and Fluorometric Methods of analysis", Part 2, F. D. Snell, 1978; (5) "Fluorometric Determination of Hydrazine and Ammonia Separately Or in Mixtures", N. D. Danielson, C. M. Conroy, Talanta, 29(5), p. 401–4, 1982; and (7) "Handbook of Anion Determination", W. J. Williams.

SYNTHETIC INDUSTRIAL WATER

Unless indicated otherwise, the water employed to prepare the synthetic industrial water solutions in the following Examples 1–9 had the following chemistry, which is prototypical of, for instance, industrial cooling waters and are thus is referred to herein as "synthetic industrial water":

200 ppm $Ca^{+2}$ (as $CaCO_3$)
200 ppm $Mg^{+2}$ (as $CaCO_3$)
200 ppm $HCO_3^-$ (as $CaCO_3$)
140 ppm $Cl^-$ (as Cl)
190 ppm $SO_4^{-2}$ (as $SO_4$)
90 ppm $Na^+$ (as Na)
pH 8.4

EXAMPLE 1

To demonstrate the application of the present process to an orthophosphate ($PO_4^{-3}$) water treatment agent, the fluorescence analysis of a series of synthetic industrial water solutions, also containing from 0 to 10.0 ppm $PO_4^{-3}$ (as $PO_4$), in the presence of an incipient reagent were conducted and percent relative fluorescence of the WTA concentration indicators in each solution were determined in comparison to such a solution without that water treatment agent. The incipient reagent was 1-pyrenesulfonic acid, employed in this Example 1 in a highly acidic vanadomolybdate aqueous solution. This solution (the fluorescent reagent) contains 1.0 ppm 1-pyrenesulfonic acid, (ppm, as acid actives), 2.35 wt./vol. percent ammonium molybdate, 0.125 wt./vol. percent ammonium metavanadate, and 33 vol./vol. percent concentrated hydrochloric acid. The fluorescent reagent (10 ml.) was admixed with 100 ml. of each of the orthophosphate-containing solutions, and the fluorescence analysis was conducted after one minute using a Gilford Fluoro IV fluorometer with dual monochromator, and a 1.0 cm×1.0 cm cuvette. An excitation wavelength of 380 nm, and an emission wavelength of 405 nm were used. The solution containing the incipient reagent not in combination with orthophosphate was assigned a percent relative fluorescence of 100. The change in the fluorescence characteristic of the incipient reagent when it interacted with the orthophosphate was a decrease in fluorescence intensity under these conditions. The fluorescence characteristic that can be correlated to the WTA concentration is the emission intensity decrease as the analyte ($PO_4^{-3}$) concentration increases. The fluorescence being measured is affected by that of the complex between incipient reagent and WTA. The concentration of $PO_4^{-3}$ versus the percent relative fluorescence determined for each sample are set forth in Table 1 below. Such data exhibits a coefficient of linear correlation (r) of 0.98. Perfect linearity would exhibit an r of 1.000.

TABLE 1

| $PO_4^{-3}$ Concentration (ppm, as $PO_4$) | Percent Relative Fluorescence |
|---|---|
| 0.0 ppm | 100% |
| 2.5 ppm | 72.6% |
| 5.0 ppm | 55.4% |
| 10.0 ppm | 29.7% |

EXAMPLE 2

To demonstrate the application of the present process to a phosphonate water treatment agent, using hydroxethylidenediphosphonic acid (HEDP), the fluorescence analysis of a series of synthetic industrial water solutions, also containing from 0.0 to 1.0 ppm phosphonate (as HEDP), in the presence of an incipient reagent were conducted and percent relative fluorescence of the WTA concentration indicators in each solution were determined in comparison to such a solution without that water treatment agent. Higher levels of phosphonate can be measured by using higher concentrations of the fluorescent reagent. The incipient reagent was 2:1 molar ratio complex bathophenanthroline:$Cu^{+2}$, employed in this Example 2 in aqueous solution. This solution (the fluorescent reagent) contained 500 ppm bathophenanthroline and 48 ppm $Cu^{+2}$ in DI water. The fluorescent reagent (2 ml.) was admixed with 100 ml. of each of the phosphonate-containing solutions, and the fluorescence analysis was conducted after one minute using a Gilford Fluoro IV dual monochromator, with a 0.2 cm diameter cuvette (flowcell). An excitation wavelength of 280 nm, and an emission wavelength of 390 nm were used. The solution containing the incipient reagent not in combination with phosphonate was assigned a percent relative fluorescence of 0. The change in the fluorescence characteristic of the incipient reagent when it interacted with the phosphonate was an increase in fluorescence intensity under these conditions. The fluorescence characteristic that can be correlated to the WTA concentration is the emission intensity increase as the analyte (HEDP) concentration increases. The concentration of phosphonate versus the percent relative fluorescence determined for each sample are set forth in Table 2 below. Such data exhibits a coefficient of linear correlation (r) of 0.9999.

TABLE 2

| Phosphonate Concentration (ppm, as HEDP) | Percent Relative Fluorescence |
|---|---|
| 0.0 ppm | 0% |
| 0.5 ppm | 24% |
| 1.0 ppm | 49% |

EXAMPLE 3

To demonstrate the application of the present process to a chromate water treatment agent, using sodium dichromate ($Na_2Cr_2O_7$), the fluorescence analysis of a series of synthetic industrial water solutions, spiked with from 0 to 18.0 ppm chromate (as $Na_2Cr_2O_7$), in the presence of an incipient reagent were conducted and percent relative fluorescence of the WTA concentration indicators in each solution were determined in comparison to such a solution without that water treatment agent. The incipient reagent was 2-naphthalenesulfonic acid (2-NSA), employed in this Example 3 in aqueous solution. This solution (the fluorescent reagent) was prepared by adding 2-NSA to DI water to form a solution containing 100 ppm 2-NSA. The fluorescent reagent (0.5 ml.) was admixed with 100 ml. of each of the chromate-containing solutions, and the fluorescence analysis was conducted after one minute using a Gilford Fluoro IV fluorometer with dual monochromator, and 0.2 cm diameter cuvette (flowcell). An excitation wavelength of 280 nm, and an emission wavelength of 330 nm were used. The solution containing the incipient reagent not in combination with chromate was assigned a percent relative fluorescence of 100. The change in the fluorescence characteristic of the incipient reagent when it interacted with the chromate was a decrease in fluorescence intensity under these conditions. The fluorescence characteristic that can be correlated to the WTA concentration is the emission intensity decrease as the analyte ($Na_2Cr_2O_7$) concentration increases. The concentration of chromate versus the percent relative fluorescence determined for each sample are set forth in Table 3 below. Such data exhibits a coefficient of linear correlation (r) of 0.998.

TABLE 3

| Chromate Concentration (ppm, as $Na_2Cr_2O_7$) | Percent Relative Fluorescence |
|---|---|
| 0.0 ppm | 100% |
| 4.5 ppm | 96.0% |
| 9 ppm | 91.9% |
| 13.5 ppm | 86.1% |
| 18.0 ppm | 82.3% |

EXAMPLE 4

To demonstrate the application of the present process to a biocide water treatment agent, using a sodium ethylene bis-dithiocarbamate product (biocide product), the fluorescence analysis of a series of synthetic industrial water solutions, spiked with from 0 to 50 ppm biocide (as biocide product), in the presence of an incipient reagent were conducted and percent relative fluorescence of the WTA concentration indicators in each solution were determined in comparison to such a solution without that water treatment agent. The incipient reagent was 2-naphthalenesulfonic acid (2-NSA), employed in this Example 4 in aqueous solution. This solution (the fluorescent reagent) was prepared by adding 2-NSA to DI water to form a solution containing 100 ppm 2-NSA. The fluorescent reagent (0.5 ml.) was admixed with 100 ml. of each of the biocide-containing solutions and the non-spiked solution, and the fluorescence analysis was conducted after one minute using a Gilford Fluoro IV fluorometer with dual monochromator, and 0.2 cm diameter cuvette (flowcell). An excitation wavelength of 280 nm, and an emission wavelength of 330 nm for the present typical concentrations of biocide (up to 50 ppm biocide product). The solution containing the incipient reagent not in combination with biocide was assigned a percent relative fluorescence of 100. The change in the fluorescence characteristic of the incipient reagent when it interacted with the biocide was a decrease in fluorescence intensity under these conditions. The fluorescence characteristic that can be correlated to the WTA concentration is the emission intensity decrease as the analyte (biocide product) concentration increases. The concentration of biocide versus the percent relative fluorescence determined for each sample are set forth in Table 4 below. Such data exhibits a coefficient of linear correlation (r) of 0.996.

TABLE 4

| Biocide Concentration (ppm, as biocide product) | Percent Relative Fluorescence |
|---|---|
| 0.0 ppm | 100% |
| 25 ppm | 83.5% |
| 50 ppm | 71.6% |

EXAMPLE 5

To demonstrate the application of the present process at higher concentrations of biocide water treatment agent, using a sodium ethylene bis-dithiocarbamate product (biocide product), the fluorescence analysis of a series of synthetic industrial water solutions, also containing from 0 to 200 ppm biocide (as biocide product), in the presence of an incipient reagent were conducted and percent relative fluorescence of the WTA concentration indicators in each solution were determined in comparison to such a solution without that water treatment agent. The incipient reagent was 2-naphthalenesulfonic acid (2-NSA), employed in this Example 5 as it was in Example 4 above, except that a different excitation wavelength was used. The fluorescent reagent (0.5 ml.) was admixed with 100 ml. of each of the spiked and non-spiked solutions, and the fluorescence analysis was conducted after one minute using a Gilford Fluoro IV fluorometer with dual monochromator, and 0.2 cm diameter cuvette (flowcell). An excitation wavelength of 310 nm, and an emission wavelength of 330 nm were used for the present higher than typical concentrations of biocide. The solution containing the incipient reagent not in combination with biocide was assigned a percent relative fluorescence of 100. The change in the fluorescence characteristic of the incipient reagent when it interacted with the biocide was a decrease in fluorescence intensity under these conditions. The fluorescence characteristic that can be correlated to the WTA concentration is the emission intensity decrease as the analyte (biocide product) concentration increases. The concentration of biocide versus the percent relative fluorescence determined for each sample are set forth in Table 5 below. Such data exhibits a coefficient of linear correlation (r) of 0.994.

TABLE 5

| Biocide Concentration (ppm, as biocide product) | Percent Relative Fluorescence |
|---|---|
| 0.0 ppm | 100% |
| 100 ppm | 83.8% |
| 200 ppm | 69.4% |

EXAMPLE 6

To demonstrate the application of the present process at low concentrations of zinc ion water treatment agent ($Zn^{+2}$), the fluorescence analysis of a series of synthetic industrial water solutions, also containing from 0.0 to 0.6 ppm zinc ion (as Zn), in the presence of an incipient reagent were conducted and percent relative fluorescence of the WTA concentration indicators in each solution was determined in comparison to such a water solution with no zinc ion. The incipient reagent was methylene blue, employed in this Example 6 as a 0.006 percent solution that contains 0.3 percent zincon in deionized water. The fluorescent reagent (0.67 ml.) was admixed with 100 ml. of each of the zinc-containing solutions and non-spiked solutions, and the fluorescence analysis was conducted after one minute using a Gilford Fluoro IV fluorometer with dual monochromator, and 0.2 cm diameter cuvette (flowcell). An excitation wavelength of 665 nm, and an emission wavelength of 690 nm were used for the present concentrations of zinc ion. The solution containing the incipient reagent not in combination with zinc ion was assigned a percent relative fluorescence of 100. The change in the fluorescence characteristic of the incipient reagent when it interacted with the zinc ion was a decrease in fluorescence intensity under these conditions. The fluorescence characteristic that can be correlated to the WTA concentration is the emission intensity decrease as the analyte (zinc ion) concentration increases. The concentration of zinc ion versus the percent relative fluorescence determined for each sample are set forth in Table 6 below. Such data exhibits a coefficient of linear correlation (r) of 0.998.

TABLE 6

| Zinc Concentration (ppm, as Zn) | Percent Relative Fluorescence |
|---|---|
| 0.0 ppm | 100% |

TABLE 6-continued

| Zinc Concentration (ppm, as Zn) | Percent Relative Fluorescence |
|---|---|
| 0.2 ppm | 88.8% |
| 0.4 ppm | 75.8% |
| 0.6 ppm | 66.7% |

EXAMPLE 7

To demonstrate the application of the present process to higher concentrations of zinc ion water treatment agent ($Zn^{+2}$), the fluorescence analysis of a series of synthetic industrial water solutions, also containing from 0.0 to 2.0 ppm zinc ion (as Zn), in the presence of an incipient reagent were conducted and percent relative fluorescence of the WTA concentration indicators in each solution was determined in comparison to such a water solution with no zinc ion. The incipient reagent was methylene blue, employed in this Example 6 again as a 0.006 percent solution that contains 0.3 percent zincon in deionized water. The fluorescent reagent (2 ml.) was admixed with 100 ml. of each of the spiked and non-spiked solutions, and the fluorescence analysis was conducted after one minute using a Gilford Fluoro IV fluorometer with dual monochromator, and 0.2 cm diameter cuvette (flowcell). An excitation wavelength of 680 nm, and an emission wavelength of 705 nm for the present concentrations of zinc ion. The solution containing the incipient reagent not in combination with zinc ion was assigned a percent relative fluorescence of 100. The change in the fluorescence characteristic of the incipient reagent when it interacted with the zinc ion was a decrease in fluorescence intensity under these conditions. The fluorescence characteristic that can be correlated to the WTA concentration is the emission intensity decrease as the analyte (zinc ion) concentration increases. The concentration of zinc ion versus the percent relative fluorescence determined for each sample are set forth in Table 7 below. Such data exhibits a coefficient of linear correlation (r) of 0.997.

TABLE 7

| Zinc Concentration (ppm, as Zn) | Percent Relative Fluorescence |
|---|---|
| 0.0 ppm | 100% |
| 1.0 ppm | 71% |
| 1.5 ppm | 60% |
| 2.0 ppm | 49% |

EXAMPLE 8

Example 8 was the same as Example 7, with the following exceptions. The Incipient Fluorescent Reagent was 1000 ppm of 4,5-dihydroxy-m-benzene disulfonic acid disodium salt monohydrate dissolved in deionized water. The Incipient Fluorescent Reagent (1.5 mL) was admixed with 100 mL of each of the molybdate-containing solutions (0.0–0.8 ppm as Mo or 0.0–1.33 ppm as $MoO_4$. The cuvette size was 1.0 cm × 1.0 cm. The excitation wavelength was 245 nm and the emission wavelength was 330 nm. The concentration of molybdate versus the percent relative fluorescence was determined for each sample and is set forth in Table 8 below. Such data exhibits a coefficient of linear correlation (r) of 0.996.

TABLE 8

| Molybdate Concentration (ppm as Mo)* | % Relative Fluorescence |
| --- | --- |
| 0.0 ppm | 100.0% |
| 0.2 ppm | 97.0% |
| 0.4 ppm | 94.0% |
| 0.6 ppm | 90.2% |
| 0.8 ppm | 88.4% |

*or 0.0–1.33 ppm (as MoO$_4$)

EXAMPLE 9

Example 9 was the same as Example 8 with the following exceptions. The Incipient Fluorescent Reagent (3.0 mL) was admixed with 100 mL of each of the molybdate-containing solutions (0.0–4.0 ppm as Mo or 0.0–6.67 ppm as MoO$_4$). The concentration of molybdate versus the percent relative fluorescence was determined for each sample and is set forth in Table 9 below. Such data exhibits a coefficient of linear correlation (r) of 0.991.

TABLE 9

| Molybdate Concentration (ppm as Mo*) | % Relative Fluorescence |
| --- | --- |
| 0.0 ppm | 100.0% |
| 1.0 ppm | 86.1% |
| 2.0 ppm | 71.6% |
| 3.0 ppm | 61.6% |
| 4.0 ppm | 54.2% |

*or 0.0–6.7 ppm (as MoO$_4$)

EXAMPLE 10

Example 10 was the same as Example 8 with the following exceptions. The Incipient Fluorescent Reagent (10.0 mL) was admixed with 100 mL of each of the molybdate-containing solutions (0.0–10.0 ppm as Mo or 0.0–16.7 ppm as MoO$_4$). The cuvette (flowcell) was 0.2 cm diameter. The concentration of molybdate versus the percent relative fluorescence was determined for each sample and is set forth in Table 10 below. Such data exhibits a coefficient of linear correlation (r) of 0.98.

TABLE 10

| Molybdate Concentration (ppm as Mo) | % Relative Fluorescence |
| --- | --- |
| 0.0 ppm | 100.0% |
| 5.0 ppm | 63.9% |
| 7.5 ppm | 52.0% |
| 10.0 ppm | 45.8% |

EXAMPLE 11

To demonstrate the application of the present invention to molybdate as a target species, the fluorescence analyses of a synthetic industrial water were conducted and percent relative fluorescence of the Target Species concentration indicators in each solution were determined in comparison to such a solution without that Target Species. Incipient reagent was 0.17% pyrocatechol violet (A.K.A. catecholsulfonephthalein) and 0.001% rhodamine WT in deionized water. The fluorescent reagent (1.00 mL) was admixed with 100 mL of each of the molybdate-containing solutions (0–4.0 ppm as Mo or 0–6.7 ppm as Mo$_4$) and the fluorescence analysis was conducted after one minute using a Gilford Fluoro IV fluorometer with dual monochromator, and 1.0 cm×1.0 cm cuvette. An excitation wavelength of 550 nm and an emission wavelength of 580 nm were used. The solution containing the fluorescent reagent but not molybdate was assigned a percent relative fluorescent of 100. The change in fluorescence character of the incipient reagent when it interacted with the molybdate was a decrease in fluorescence intensity under these conditions. The fluorescence character that can be correlated to the Target Species concentration is the emission intensity decrease as the molybdate increases. The concentration of molybdate versus the percent relative fluorescence was determined for each sample and is set forth in Table 11 below. Such data exhibits a coefficient of linear correlation (r) of 0.99.

TABLE 11

| Molybdate Concentration (ppm as Mo)* | % Relative Fluorescence |
| --- | --- |
| 0.0 ppm | 100.0% |
| 1.0 ppm | 85.2% |
| 2.0 ppm | 66.1% |
| 3.0 ppm | 55.0% |
| 4.0 ppm | 46.5% |

*or 0.0–6.7 ppm (as Mo$_4$)

EXAMPLE 12

To demonstrate the application of the present invention to Total Alkalinity as a target species, the fluorescence analysis of a synthetic industrial water were conducted and percent relative fluorescence of the Target Species concentration indicators in each solution were determined in comparison to such a solution without that Target Species. Incipient fluorescent reagent was 1000 ppm of 4-aminobenzoic acid in deionized water. The fluorescent reagent (0.1 ml) was added to 100 mL of each of the target-containing solutions. The fluorescence analysis was conducted with a Gilford Fluoro IV fluorometer with dual monochromator, and 0.2 cm diameter cuvette (flow cell). An excitation wavelength of 275 nm and an emission wavelength of 340 nm were used. The solution containing the fluorescent reagent but 0 ppm (bi)carbonate alkalinity was assigned a percent relative fluorescence of 0% and solution containing fluorescent reagent between pH 6.4–8.9 (without any sulfuric acid neutralizing agent present) was assigned a percent relative fluorescence of 100%. The change in fluorescence character of the incipient reagent was measured after one minute and as it interacted with the total alkalinity was an increase in fluorescence intensity under these conditions. The fluorescence character that can be correlated to the Target Species concentration is the emission intensity increase as the analyte increases. The concentration of Total Alkalinity versus the percent relative fluorescence was determined for each sample and is set forth in Table 8 below.

TABLE 12

| Total alkalinity Added (as CaCO3) | % Relative Fluorescence |
| --- | --- |
| 200 ppm (initial) | 4.0% |
| 250 ppm | 8.6% |
| 275 ppm | 14.7% |
| 300 ppm | 85.8% |
| 325 ppm | 91.6% |

An appearance or disappearance of fluorescence, a shift in excitation and/or emission wavelengths of fluorescence, fluorescence quenching and fluorescence changes based on light absorbance changes are phenomena which may develop upon the interaction of a polymeric WTA and a "fluorochromatic" reagent. The use of a fluorescent reagent as the incipient reagent for polymeric WTA's is described in more detail below.

A method for determining the concentration of sulfonate and/or polycarboxylate compounds in a solution sample by adding a metachromatic dye thereto and then comparing the solution's absorbance to that of standard solutions is described in U.S. Pat. No. 4,894,346, Myers et al., issued Jan. 16, 1990, incorporated hereinto by reference. Such a technique, however, is not a fluorescence analysis technique.

Some dyes exhibit a fluorochromatic response (fluorescence change) in the presence of polymeric species. It has been observed that the fluorescence intensity of certain polycyclic aromatic dyes increased when they interacted with various cationic or nonionic polymers, and a secondary method utilizes this phenomenon and the affinity of the resulting complexes to biological polyanions to form ternary complexes for use in fluorescence microscopy, flow cytometry and other quantitative method, as described in European Patent No. 0 231 127, A. L. Wu, 1987, incorporated hereinto by reference.

Another quantitative method employs the complexing interaction between an anionic dye and a cationic polyelectrolyte (but not the metachromatic spectral change), whereby a complex that can be extracted with a hydrophobic solvent is formed, as is described in Anal. Chem., D. P. Parazak, C. W. Burkhardt and K. J. McCarthy, Vol. 59, pages 1444–1445, 1987, incorporated by reference.

The present invention might also employ fluorochromatic reagents. A fluorochromatic reagent is fluorescent, and hence is a compound that absorbs light of a given wavelength and emits it, or fluoresces, at a longer wavelength. The main structural unit of a fluorescent reagent, which is always unsaturated, is called the fluorophore. Fluorochromatic reagents are ionic, fluorescent dyes that interact with oppositely charged polyelectrolytes whereby the intensity of their fluorescent emissions at their normal peak emission wavelength is changed. It has been found that, in a reasonably dilute aqueous solution containing a polyelectrolyte, a fluorochromatic reagent will exhibit one of several types of polyelectrolyte-concentration-dependent behaviors. These behavior types can be classified by the behavioral effect seen when polyelectrolyte concentration increases as follows:

(A) less intense emission when measured about a given emission wavelength peak;

(B) more intense emission when measured about a given emission wavelength peak; and (C) the appearance of a new emission peak and a more intense emission when measured about the new emission wavelength peak.

The type of behavior shown is dependent upon the chemical structure of the fluorochromatic reagent and/or the polyelectrolyte/fluorochromatic reagent ratio. The decrease in the intensity of the fluorescence emissions at a normally peak emission wavelength (Type A behavior) seen in some fluorochromatic reagents has been found to be an emission quenching phenomenon, and such phenomenon can be considered a fluorochromatic quenching. The decrease in the intensity of the fluorescence emissions at a normally peak emission wavelength seen in other fluorochromatic reagents has been found to be an emission wavelength shift phenomenon (Type C behavior), and such phenomenon can be considered a fluorochromatic shift. Type C behavior includes not only such emission wavelength shifting phenomenon but also the appearance of fluorescence (the new emission wavelength peak) in a previously weak or substantially nonfluorescent compound. Only a fraction of metachromatic dyes also exhibit fluorochromatic behavior and fluorochromatic reagents may or may not exhibit visible metachromatic behavior. The metachromatic behavior and the fluorochromatic behavior are distinct spectral phenomena. The wavelength of maximum fluorescence excitation may or may not be the wavelength of maximum absorption of some dyes and is a wavelength distinct from, and unrelated to, the wavelength of maximum absorption of other dyes.

Fluorochromatic reagents include, but are not limited to, Methylene Blue, Nile Blue A and pinacyanol chloride.

There is an ionic site to fluorochromatic reagent mole ratio limit to this determination. This determination is dependent upon an interaction between fluorochromatic reagent and polyelectrolyte ionic sites, which interaction for example decreases the fluorescent intensity at the selected emission wavelength (Type A behavior). When that limit is exceeded, the fluorochromatic reagent available for interacting with the ionic sites can be considered exhausted. The slope of the plot of emission intensity versus polyelectrolyte concentration levels off when this ratio limitation is met, and the standard curve no longer provides the desired correlation between fluorescent emission intensity and polyelectrolyte concentration. Higher concentrations of polyelectrolyte can be measured by increasing the concentration of the fluorochromatic reagent. The ionic site to fluorochromatic dye mole ratio limitation can be determined empirically for any desired combination of polyelectrolyte and fluorochromatic reagent, or it can be estimated based on a known or estimated charge density of the polyelectrolyte. A prudent estimate of the ionic site to fluorochromatic reagent mole ratio limit may presume that the limit will fall above a 1:1 mole ratio and set the limitation at the estimated 1:1 mole ratio to assure the limitation is not exceeded, although it is believed that for most Type A behavior polyelectrolyte/fluorochromatic reagent combinations the actual limit will be found within the range of from about 1.2:1 to about 1.5:1 mole ratio of polyelectrolyte ionic sites to fluorochromatic reagent.

The amount of fluorochromatic reagent added to the sample preferably should be selected to avoid the ionic site to fluorochromatic reagent mole ratio limitation, based on the probable polyelectrolyte concentration range to be encountered at a given site. If desired, a polyelectrolyte concentration determination can be easily confirmed by this method, using a duplicate sample, less fluorochromatic reagent and a second standard curve based on the lesser amount of fluorochromatic reagent. Comparable test results confirm that the ionic site to fluorochromatic reagent mole ratio limitation has not been reached.

As noted above, the decrease in emission intensity at the selected wavelength, which preferably should be at or about an emissions peak for the given fluorochromatic reagent in the absence of polyelectrolyte, may be due to a fluorochromatic quenching or a fluorochromatic wavelength shift, and the possibility of both phenomena occurring in some fluorochromatic reagents cannot be excluded. Which phenomenon is occurring is believed dependent on the fluorochromatic reagent selected. Most advantages of the present invention can be realized regardless of which phenomenon is occurring. Nonetheless, in preferred embodiment the fluorochromatic reagent employed is one that provides a change in fluorescent emission intensity at the selected wavelength due to fluorochromatic wavelength shift.

WTA-FEED TRACERS

By the terms "tracing" is meant herein, unless expressly indicated otherwise, the determination of the concentration of an inert tracer(s) in the water system. Such tracing would seldom be conducted on a singular, intermittent or semi-continuous basis for the purpose of the present invention, but instead on a substantially continuous basis, and preferably the concentration determination is conducted on-site (at the site of the water system) to provide rapid determinations of WTA feed rate and consumption rate. Inert tracers are at times referred to herein as a "tracer".

Generally, the dosage of a tracer to a WTA feed will be at least sufficient to provide a concentration of tracer at the downstream sampling/monitoring station of at least about 50 ppt, and more commonly at least about 5 ppb or higher, up to about 100 or 1000 ppm, in the water system.

The WTA feed is commonly, but not always, comprised of the active WTA and one or more inert diluents. A diluent is frequently a solvent for the WTA, and such solvent can be, and in many instances is, water. A diluent is frequently included in the WTA feed to facilitate the rapid and substantially homogeneous distribution of the active WTA in the water system to which the WTA feed is charged. The concentration of the active WTA in the WTA feed is generally from about 0.5 to about 50 weight percent and at times higher. The weight ratio of active WTA to tracer in the WTA feed is often within the range of from about 10:1 to about 1000:1. When the tracer is a part of the active WTA, for instance a fluorescent pendant substituent of an active water treatment polymer, the range above would be based on total weight of the WTA (including the tagging substituent) to the weight of the tagging substituent. The weight ratio between the active WTA and the tracer in a system ahead of any selective WTA-consuming site is of course substantially the same as that of the WTA feed, and thereafter that weight ratio would fall as the WTA is selectively consumed in the water system, for instance to the extent of approaching a 1:1 weight ratio or less.

The tracer is preferably selected from among those that are easily quantifiable by a fluorescence analysis method, a preferred analytical technique for the purposes of the present system. Other analysis methods not excluded for use in quantifying the tracer are HPLC and fluorescence analysis combinations, which are described in more detail elsewhere herein.

An inert tracer must be both soluble and stable in the WTA feed and transportable with the water of the water system and thus wholly water-soluble or dispersable therein at the concentration it is used, under the temperature and pressure conditions to be encountered. Preferably, the selected inert tracer also meets the following criteria:

1. Be thermally stable and not decompose at the temperature within the given system;
2. Be detectable on a continuous or semicontinuous basis and susceptible to concentration measurements that are accurate, repeatable and capable of being performed on system water;
3. Be substantially foreign to the chemical species that are normally present in the water of the water systems in which the inert tracer may be used;
4. Be substantially impervious to interference from, or biasing by, the chemical species that are normally present in the water of the water systems in which the inert tracer may be used;
5. Be substantially impervious to any of its own potential specific losses from the water of the water system, including selective carry-over;
6. Be compatible with all treatment agents employed in the water of the water systems in which the inert tracer may be used, and thus in no way reduce the efficacy thereof;
7. Be compatible with all components of the WTA feed formulation despite the concentrations of the tracer and/or other components in such a formulation, and despite any storage and/or transportation conditions encountered; and
8. Be reasonably nontoxic and environmentally safe, not only within the environs of the water of the water system in which it may be used, but also upon discharge therefrom.

The chemical compound(s) selected as an inert tracer(s) should not be one that is consumed or selectively lost to the water of the water system, for instance due to degradation, deposition, complexation, or other phenomena, unless such loss is at a rate that is predictable and proportional to a system-consumption loss of the WTA being monitored. An inert tracer(s) used in the present invention is preferably substantially unconsumed in the water system environment. An inert tracer(s) that is wholly inert in the water system environment would not react with any of the components in the water of the water system to which it is added, would not degrade in the environment of the water of the water system, would be incapable of coupling and/or depositing in any manner within such system and would not appreciably be effected by other system parameters such as metallurgical composition, heat changes or heat content. There are water-soluble inert tracer(s) that are wholly inert, or substantially inert, in the aqueous environments likely to be encountered in industrial water systems. Further, it is believed that an inert tracer(s) having a degree of inertness such that no more than 10 weight percent thereof is lost due to reaction, degradation, coupling and/or deposition during the time that elapses between its addition and its final monitoring as a system component, is sufficiently, or substantially, inert for the purpose of the present invention for most, if not all, WTA feed monitorings.

As noted above, an inert tracer must be added to the WTA feed in known proportion to the WTA, and preferably an inert tracer is introduced into the water system together or separately with the WTA feed at a known and constant concentration therein which is at a known and constant proportion to the WTA actives therein. The preferred method of achieving such proportionality is to formulate an inert tracer together with WTA concentrate if the WTA feed is to be prepared by on-site dilution and if an inert tracer is stable in such concentrate. The concentrate may be an aqueous solution or other substantially homogeneous admixture that disperses with reasonable rapidity in the dilution fluid which is added. Since in most any instance a WTA and an inert tracer would both be added to a system as components of a fluid feed formulation, rather than as a dry solid or individual neat liquids, the tracer concentration may be correlated not to the numerical concentration of an inert tracer itself or the WTA itself, but instead to the concentration of a formulated product containing the WTA, which in turn can be correlated to the concentration of an inert tracer and/or WTA when and if such information is required. Therefore, the proportionality of the tracer to the WTA feed for the purposes of the present invention can be equivalent to a proportionality of tracer to the active WTA component of the feed. The correlation between inert tracer concentration and WTA concentration is of course a correlation based on zero-concentration consumption of WTA.

Among the substantially water-system inert fluorescent compounds are the mono-, di- and trisulfonated naphthalenes, including their water-soluble salts, particularly the various naphthalene mono- and disulfonic acid isomers, which are preferred inert tracers for use in the present invention. The naphthalene mono- and disulfonic acid isomers are water-soluble, generally available commercially and easily detectable and quantifiable by known fluorescence analysis techniques. Preferred naphthalene mono- and disulfonic acid isomers are the water-soluble salts of naphthalene sulfonic acid ("NSA"), such as 1-NSA and 2-NSA, and naphthalene disulfonic acid ("NDSA" or "NDA"), for instance 1,2-NDSA, 1,3-NDSA, 1,4-NDSA, 1,5-NDSA, 1,6-NDSA, 1,7-NDSA, 1,8-NDSA, 2,3-NDSA, 2,4-NDSA and so forth. Many of these inert tracer(s) (mono-, di- and trisulfonated naphthalenes and mixtures thereof) are extremely compatible with the environments of most systems. Among these preferred fluorescent tracers, 2-NSA and 1,5-NDSA have been found to be thermally stable (substantially inert) at temperatures up to at least about 540° C. (1004° F.), for at least 24 hours at 285° C. (545° F.) and at pressures up to about 1,500 psig for time periods at least commensurate with, and often well in excess of, commercial water system holding times. Such inert fluorescent tracers are not volatized into steam.

Another group of inert fluorescent tracers that are preferred for use in the process of the present invention are the various sulfonated derivatives of pyrene, such as 1,3,6,8-pyrene tetrasulfonic acid, and the various water-soluble salts of such sulfonated pyrene derivatives.

In preferred embodiment an inert tracer is one of these sulfonated fluorescent tracers and is employed at concentration levels of from about 0.5 ppb, and more commonly at least about 5 ppb or higher, up to about 10 ppm in the water system.

Fluorescent chemical tracers and monitoring techniques are now known, for instance as disclosed in U.S. Pat. No. 4,783,314, J. E. Hoots and B. E. Hunt, issued Nov. 8, 1988, incorporated herein by reference, wherein fluorescent tracers are employed in combination with a fluorescence monitoring, such as the sodium salt of 2-naphthalenesulfonic acid.

When the tracer is 2-NSA, one of the water-soluble salts of naphthalene sulfonic acid ("NSA"), its concentration in the water system can be fluorometrically measured by excitation at 277 nm and emission measurement at 334 nm, and the emissions observed referenced to a standard aqueous solution containing 0.5 ppm 2-NSA, as acid actives.

An inert tracer may be any chemical specie that is sufficiently water soluble and can be monitored in the water system with sufficient ease for the purposes of the present invention. Active tracer chemicals may be lost to a water system due to both selective and hydraulic losses. In comparison, inert tracers are lost to a water system substantially only due to hydraulic losses such as removal as part of the blowdown. For the purposes of the present invention, a tracer used as an inert tracer for the purposes of the present invention may be selectively lost to the water system in any amount by any mechanism, provided that such selective loss occurs downstream of the monitoring for such tracer.

A tracer may be an active tracer in one system, and an inert tracer in another. An active tracer may be, for instance, a corrosion inhibitor. One series of compounds applied to reduce copper and copper-alloy corrosion are aromatic organic corrosion inhibitors. This series of organic compounds, which includes benzotriazole ("BT"), butylbenzotriazole ("BBT"), tolyltriazole ("TT"), and related compounds, react with the metal surface and form protective films on copper and copper alloys. These compounds are active corrosion inhibition treatment components and are referred to generally herein as copper corrosion inhibitors or corrosion inhibitors, or as aromatic azoles, and at times as triazoles or aromatic(thi)(tri)azoles. The preferred analytical technique for aromatic(thi)(tri)azoles when used as a tracer in the process of the present invention is fluorescence emission spectroscopy, which is described in U.S. patent application Ser. No. 07/872,624, filed on Apr. 22, 1992, now U.S. Pat. No. 5,278,074 incorporated hereinto by reference.

Some water systems have no copper, copper alloy or other metal surfaces that require protection from a corrosion inhibitor, and for such systems the use of copper corrosion inhibitors as WTA-feed tracers for the purposes of the present invention would generally an uncommon, but not excluded, embodiment of the invention. The use of copper corrosion inhibitors may nonetheless be a preferred embodiment in such systems when they are already contained in waters that will make up at least a portion of the WTA-feed stream or when water from the system will be recycled to a system that needs such corrosion inhibitor. For instance, some industries may recycle water from one water system, such as a cooling tower, through another water system. In such instances, if these copper corrosion inhibitors were added to the water of the first water system for corrosion inhibition and/or tracer performance, they may be present in the WTA-feed stream of the second water system in sufficient concentration for the purposes of the present invention. Further, if the second water system contains no metal surfaces which lead to consumption of such copper corrosion inhibitors, or at least no such metal surfaces upstream of relevant monitorings, such normally "active" tracers are inert tracers for the purposes of the present invention. For example, if the relevant monitorings were of the WTA-feed stream (to determine the feed concentration of the inert tracer) and a site along the body of the water system, and there were no metal surfaces leading to consumption between these points, the copper corrosion inhibitors would be inert tracers.

The use of other tracers may similarly become a preferred embodiment of the present invention when they are already contained in waters that will make up at least a portion of the WTA-feed stream or when the inert tracer-containing effluent water will be recycled to a system that employs such tracer as a tracer or for other purposes, such as treatment purposes.

Certain fluorescent compounds change their fluorescence intensity as measured at a given emission wavelength in response to one or more conditions of the environment, which may be an in-system environmental condition. The present invention does not exclude tracer monitoring techniques that comprise or include a change in fluorescence intensity, which is a technique of fluorescence emission spectroscopy as that terminology is used herein.

The terms "in-system WTA concentration indicator", "WTA concentration indicator" and "WTA indicator" are used herein interchangeably, and there is no definition significance in the choice of variant employed. The term "in-system concentration" in all instances refers to the concentration of a specie(s) within the water of a water system, to the exclusion of any amount of such specie(s) not dispersed within the water, regardless of whether such excluded amount is in contact with such water, for instance as a deposit formed on a surface in contact with such water.

Unless expressly indicated otherwise herein, the inclusion of a prefix or suffix in parenthesis designates the word with such prefix or suffix as an alternative. For instance, "specie(s)" means "specie and/or species", "(meth)acrylamide" means "acrylamide and/or methacrylamide", "determination(s)" means "determination and/or determinations", "technique(s)" means "technique and/or techniques", "location(s)" means, "chemical(s)" means "chemical and/or chemicals", "component(s)" means "component and/or components", "tracer(s)" means "tracer and/or tracers", and the like. By "ppm" is meant "parts per million" by weight. By "ppb" is meant "parts per billion" by weight. By "ppt" is meant "parts per trillion" be weight.

INDUSTRIAL APPLICABILITY OF THE INVENTION

The present invention is applicable to industries employing water treatment agents for the treatment of aqueous systems, mixed aqueous/nonaqueous systems and substantially nonaqueous system, including industries employing boiler water systems, cooling water systems, and so forth.

We claim:

1. A method of concentration-consumption responsive regulation of water treatment agent feed comprising:
   drawing a sample of fluid from an industrial fluid system containing a substantially nonfluorescent water treatment agent;
   adding to said sample an incipient reagent in an amount effective to form a concentration indicator comprising a reaction product of said incipient reagent and said substantially nonfluorescent water treatment agent;
   monitoring said concentration indicator by fluorescence analysis of said sample to determine at least one fluorescence emission value that can be correlated to an in-system concentration of said water treatment agent;
   correlating said fluorescence emission value to said in-system concentration of said water treatment agent; and
   regulating a feed of said water treatment agent to said fluid system based on said in-system concentration of said water treatment agent.

2. The method of claim 1 wherein said correlation of said fluorescence emission value to said in-system concentration of said water treatment agent is established by at least one difference between at least one fluorescence characteristic of said incipient reagent and on fluorescence characteristic of said concentration indicator.

3. The method of claim 1 wherein said monitoring is conducted at the site of said industrial system on a substantially continuous basis.

4. The method of claim 1 wherein said incipient reagent is substantially nonfluorescent and said concentration indicator is fluorescent.

5. The method of claim 1 wherein said incipient reagent is fluorescent and said concentration indicator is substantially nonfluorescent.

6. The method of claim 1 wherein both the incipient reagent and concentration indicator are fluorescent, said fluorescence analysis is performed using a fluorescence analysis technique, that at least minimizes interference between fluorescence emission of any residual incipient reagent and fluorescence emissions of said concentration indicator.

7. The method of claim 1 further including feeding said water treatment agent to said fluid system and monitoring the rate of said water treatment agent feed by fluorescence analysis.

8. The method of claim 1 further including feeding said water treatment agent to said fluid system and monitoring the rate of said water treatment agent feed by fluorescence analysis by:
   (1) feeding said water treatment agent through a feed line to said fluid system as a component of a treatment product which contains an inert fluorescence tracer in known proportion to said water treatment agent,
   (2) determining the concentration of said tracer in said feed line or within said system to determine a system consumption of said water treatment agent; and
   (3) controlling the feed of the water treatment agent to control the system consumption within a predetermined range.

9. The method of claim 1 further including feeding said water treatment agent to said fluid system and monitoring the rate of said water treatment agent feed by fluorescence analysis by:
   (1) feeding said water treatment agent through a feed line to said fluid system as a component of a treatment product which contains a fluorescent-tagged component, and
   (2) determining the concentration of said fluorescent-tagged component in said feed line.

10. The method of claim 1 wherein said in-system concentration of said water treatment agent is effected by the formation and/or dissolution of deposits containing said water treatment agent within said system, and said formation and dissolution of said deposits is related to the performance of a water treatment program, whereby said regulating of said water treatment agent feed is also a regulation of water treatment agent feed based on water treatment program performance.

11. The method of claim 1 wherein said substantially nonfluorescent water treatment agent is selected from the group consisting of $Zn^{+2}$ compounds, orthophosphates, condensed inorganic phosphates, phosphonates, boron compounds, alkalinity agents, molybdate compounds, silica compounds, non-oxidizing biocides, surfactants, neutralizing amines, oxygen scavengers, organic polymers, and chelants.

12. The method of claim 1 wherein said fluid system is an industrial water system comprised of at least about 70 weight percent water.

13. The method of claim 1 wherein said system is an industrial cooling water system or an industrial boiler water system.

14. The method of claim 1 wherein said system contains a plurality of water treatment agents and in-system concentrations for said plurality of water treatment agents are determined by monitoring a plurality of concentration indicators.

15. The method of claim 1 wherein said system is a mixed aqueous/nonaqueous fluid system.

16. The method of claim 1 wherein said analysis is performed without isolating said concentration indicator.

17. The method of claim 1 wherein said in-system concentration of said water treatment agent is a residual concentration of said water treatment agent in solute form in said system, and wherein said water treatment agent has an established target and/or optimal residual concentration for said system.

18. The method of claim 1 wherein said system is a nonaqueous fluid system.

* * * * *